（12) United States Patent
Topilko et al.

US012052979B2

(10) Patent No.: US 12,052,979 B2
(45) Date of Patent: Aug. 6, 2024

(54) TRANSGENIC MOUSE MODEL OF NEUROFIBROMATOSIS TYPE 1

(71) Applicants: PARIS SCIENCES ET LETTRES—QUARTIER LATIN, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR)

(72) Inventors: Piotr Topilko, Boullay-les-Troux (FR); Patrick Charnay, Bourg-la-reine (FR); Fanny Coulpier, Saint-Maurice (FR); Aurélie Gresset, Fontenay-aux-Roses (FR); Katarzyna Radomska, Paris (FR)

(73) Assignees: 1. PARIS SCIENCES ET LETTRES—QUARTIER LATIN, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR)

( * ) Notice: Subject to any disclaimer, the term of this patent is extended or adjusted under 35 U.S.C. 154(b) by 824 days.

(21) Appl. No.: 16/625,999

(22) PCT Filed: Jun. 29, 2018

(86) PCT No.: PCT/EP2018/067675
§ 371 (c)(1),
(2) Date: Dec. 23, 2019

(87) PCT Pub. No.: WO2019/002590
PCT Pub. Date: Jan. 3, 2019

(65) Prior Publication Data
US 2021/0153485 A1    May 27, 2021

(30) Foreign Application Priority Data
Jun. 29, 2017  (EP) .................................... 17305822

(51) Int. Cl.
*A01K 67/027*   (2024.01)
*A01K 67/0276*  (2024.01)
*A61K 49/00*    (2006.01)
*C12N 5/09*     (2010.01)
*G01N 33/50*    (2006.01)

(52) U.S. Cl.
CPC ...... *A01K 67/0276* (2013.01); *A61K 49/0008* (2013.01); *C12N 5/0693* (2013.01); *G01N 33/5044* (2013.01); *A01K 2217/054* (2013.01); *A01K 2217/206* (2013.01); *A01K 2227/105* (2013.01); *A01K 2267/0331* (2013.01); *G01N 2500/10* (2013.01)

(58) Field of Classification Search
None
See application file for complete search history.

(56) References Cited

U.S. PATENT DOCUMENTS

| 6,172,188 B1 | 1/2001 | Thastrup et al. |
| 2005/0186184 A1 | 8/2005 | Topilko et al. |
| 2011/0035815 A1 | 2/2011 | Zong et al. |

FOREIGN PATENT DOCUMENTS

WO    2016/077429 A1    5/2016

OTHER PUBLICATIONS

Gresset (Stem Cell Reports, 2015, vol. 5, p. 278-290) plus Supplemental Materials.*
Zhu, Science, 2002, vol. 296, No. 5569, p. 920-922.*
Nf1 flox Strain Details by Jackson Labs.*
MGI website definition of "floxed".*
Bajenaru (Am. Soc. for Microbiol. Mol. and Cell. Biol., 2002, vol. 22, No. 14, p. 5100-5113).*
Radomska (Cancer Disc., 2019, vol. 9, No. 1, p. 130-147).*
Gresset (Stem Cell Reports, 2015, vol. 5, p. 278-290, plus supplemental materials) (Year: 2015).*
Gutmann et al., "Mouse Models of Neurofibromatosis 1 and 2", Neoplasia, Jul. 2002; 4(4): 279-290, 12 pgs.
Gresset et al., "Boundary caps give rise to neurogenic stem cells and terminal glia in the skin", Stem Cell Reports, Aug. 11, 2015; 5(2):278-90, 13 pgs.
Shimshek et al., "Codon-improved Cre recombinase (iCre) expression in the mouse", Genesis, Jan. 2002;32(1):19-26, 8 pgs.
Eroshenko & Church, "Mutants of Cre recombinase with improved accuracy", Nat Commun, 2013; 4:2509, 22 pgs.
Nagy, "Cre recombinase: the universal reagent for genome tailoring." Genesis. Feb. 2000; 26(2):99-109, 11 pgs.
Joseph et al., "Neural crest stem cells undergo multilineage differentiation in developing peripheral nerves to generate endoneurial fibroblasts in addition to Schwann cells", Development, Nov. 2004; 131(22):5599-612, 33 pgs.

(Continued)

*Primary Examiner* — Michael C Wilson
(74) *Attorney, Agent, or Firm* — Maier & Maier, PLLC

(57) ABSTRACT

A transgenic non-human animal model for Neurofibromatosis type 1, wherein the Nf1 gene is specifically inactivated in BC cells and derivatives thereof. Also, an in vitro method of producing cutaneous and plexiform Neurofibromas (NFBs) and/or for studying the development and composition of plexiform NFBs, including culturing in vitro Prss56-expressing cells and-derivatives thereof obtained from the transgenic non-human animal model. Further, a method for screening a candidate compound for use as a drug to treat Neurofibromatosis type 1, cutaneous NFBs and/or plexiform NFBs including contacting the candidate compound Prss56-expressing cells and-derivatives thereof obtained from the transgenic non-human animal model or administering the candidate compound to the transgenic non-human animal model.

7 Claims, 16 Drawing Sheets
Specification includes a Sequence Listing.

(56) References Cited

OTHER PUBLICATIONS

Madisen et al., "A robust and high-throughput Cre reporting and characterization system for the whole mouse brain", Nat Neurosci, Jan. 2010; 13(1):133-40, 26 pgs.
Mata et al., "S100 is preferentially distributed in myelin-forming Schwann cells", J Neurocytol, Jun. 1990; 19(3):432-42, 11 pgs.
Wu et al., "Plexiform and dermal neurofibromas and pigmentation are caused by NF1 Loss in Desert Hedgehog-Expressing Cells", Cancer Cell. Feb. 2008; 13(2):105-16, 26 pgs.
Carroll, "Molecular mechanisms promoting the pathogenesis of Schwann cell neoplasms", Acta Neuropathol, 2012, 123:321-348, 28 pgs.
Jessen et al., "MEK inhibition exhibits efficacy in human and mouse neurofibromatosis tumors", J Clin Invest. Jan. 2013; 123(1):340-7, 8 pgs.
Prada et al., "Neurofibroma-associated macrophages play roles in tumor growth and response to pharmacological inhibition", Acta Neuropathol. Jan. 2013; 125(1):159-68, 10 pgs.
Joseph et al., "The loss of Nf1 transiently promotes self-renewal but not tumorigenesis by neural crest stem cells", Cancer Cell. Feb. 2008; 13(2):129-40, 30 pgs.
Zhu et al., "Ablation of NF1 function in neurons induces abnormal development of cerebral cortex and reactive gliosis in the brain", Genes Dev. Apr. 1, 2001; 15(7):859-76, 18 pgs.
Zhu et al., "Neurofibromas in NF1: Schwann cell origin and role of tumor environment", Science. May 3, 2002; 296(5569):920-2, 4 pgs.
Parrinello & Lloyd. "Neurofibroma development in NF1-insights into tumour initiation." Trends Cell Biol. Aug. 2009; 19(8): 395-403, 9 pgs.
International Search Report dated Jul. 27, 2018, in connection with corresponding international application No. PCT/EP2018/067675, 8 pgs.

\* cited by examiner

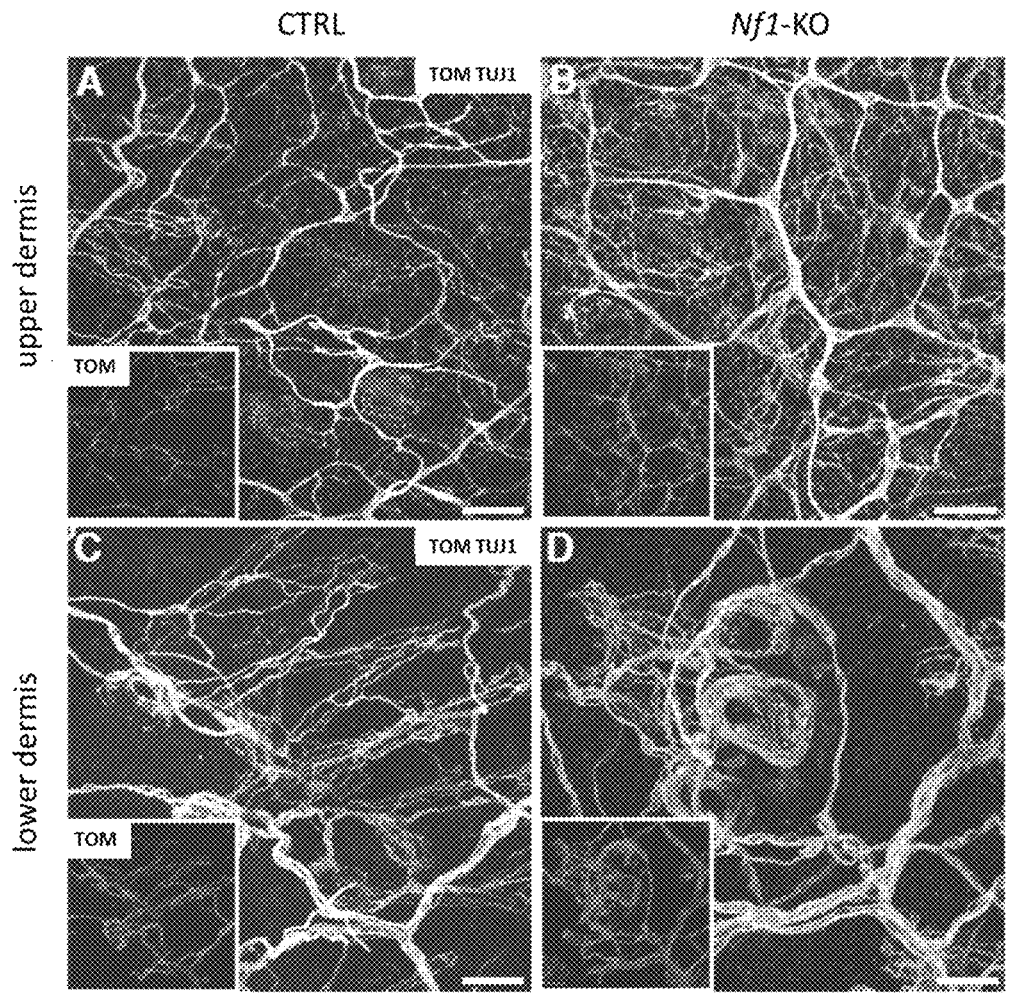
FIG. 9A-D

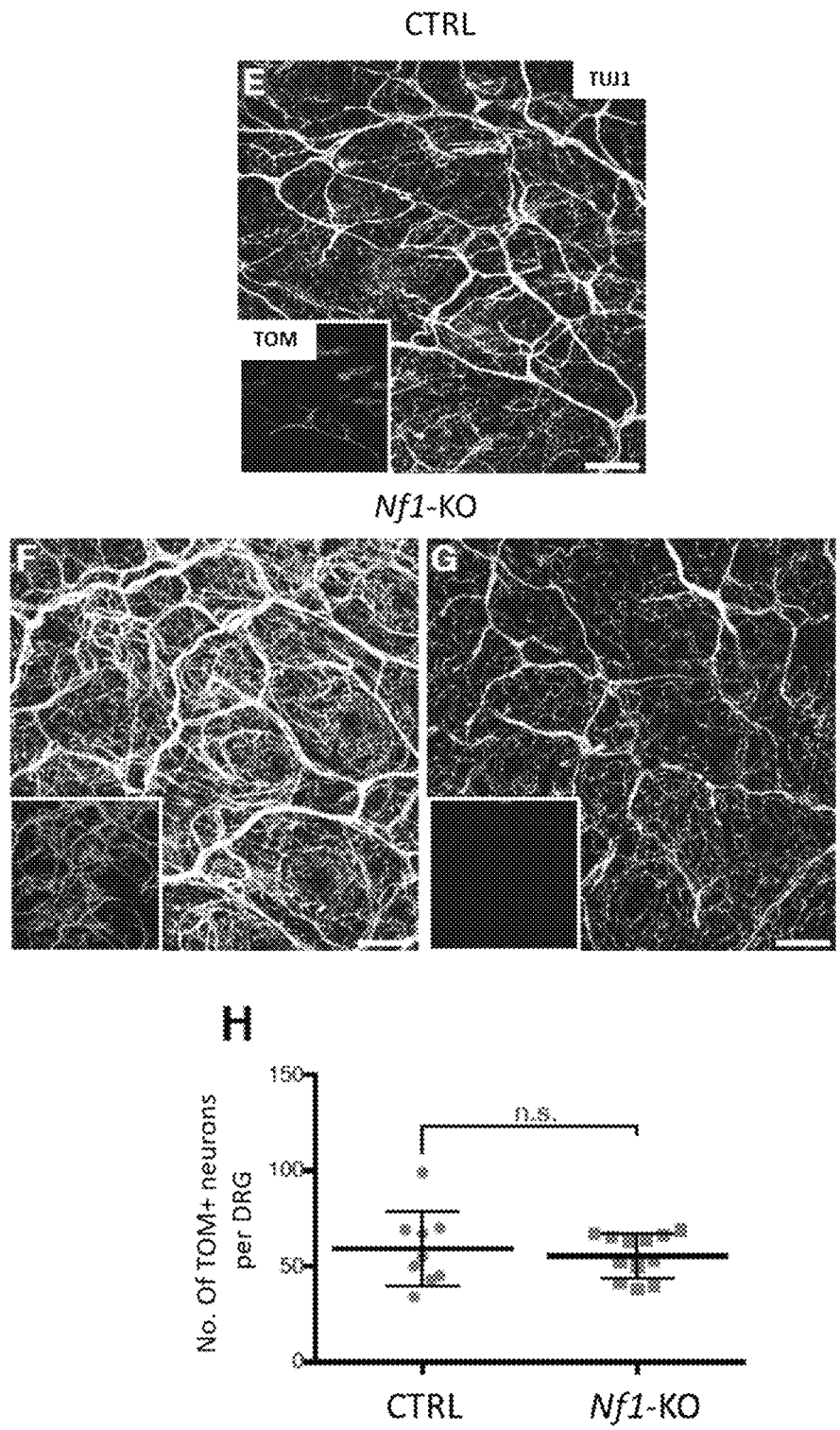
FIG. 9E-H

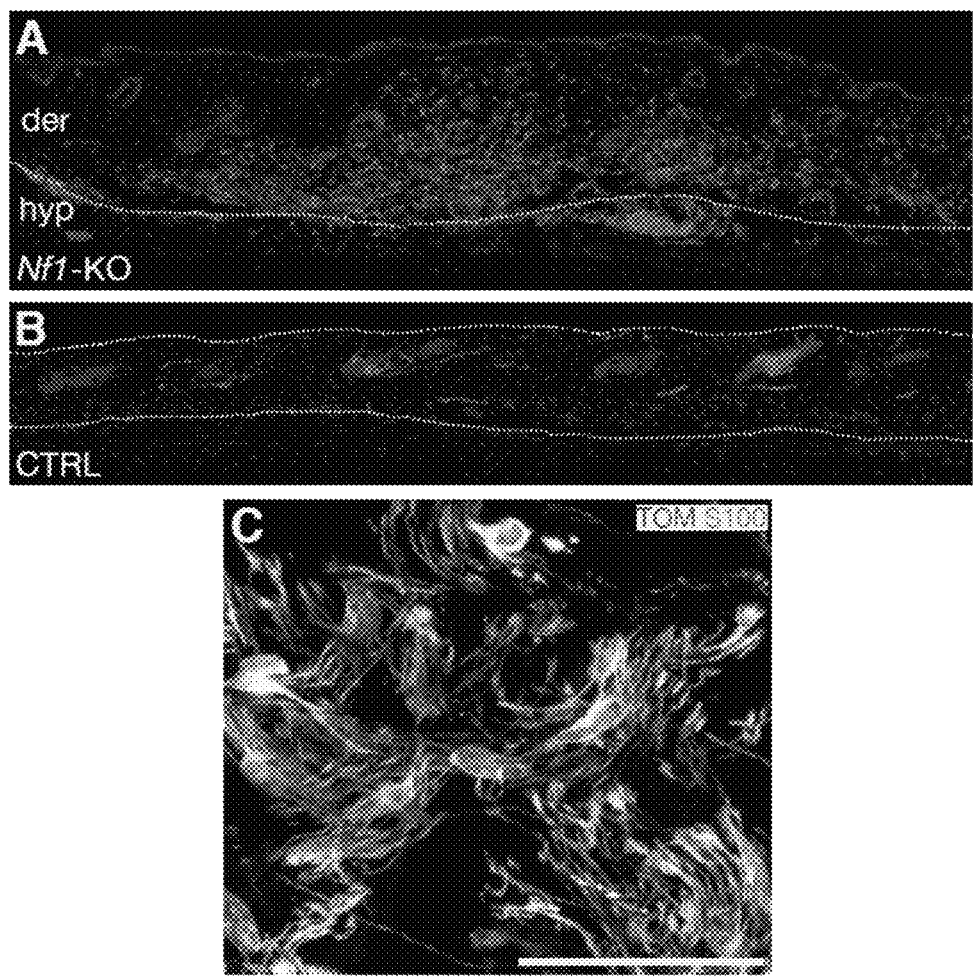
FIG. 10A-C

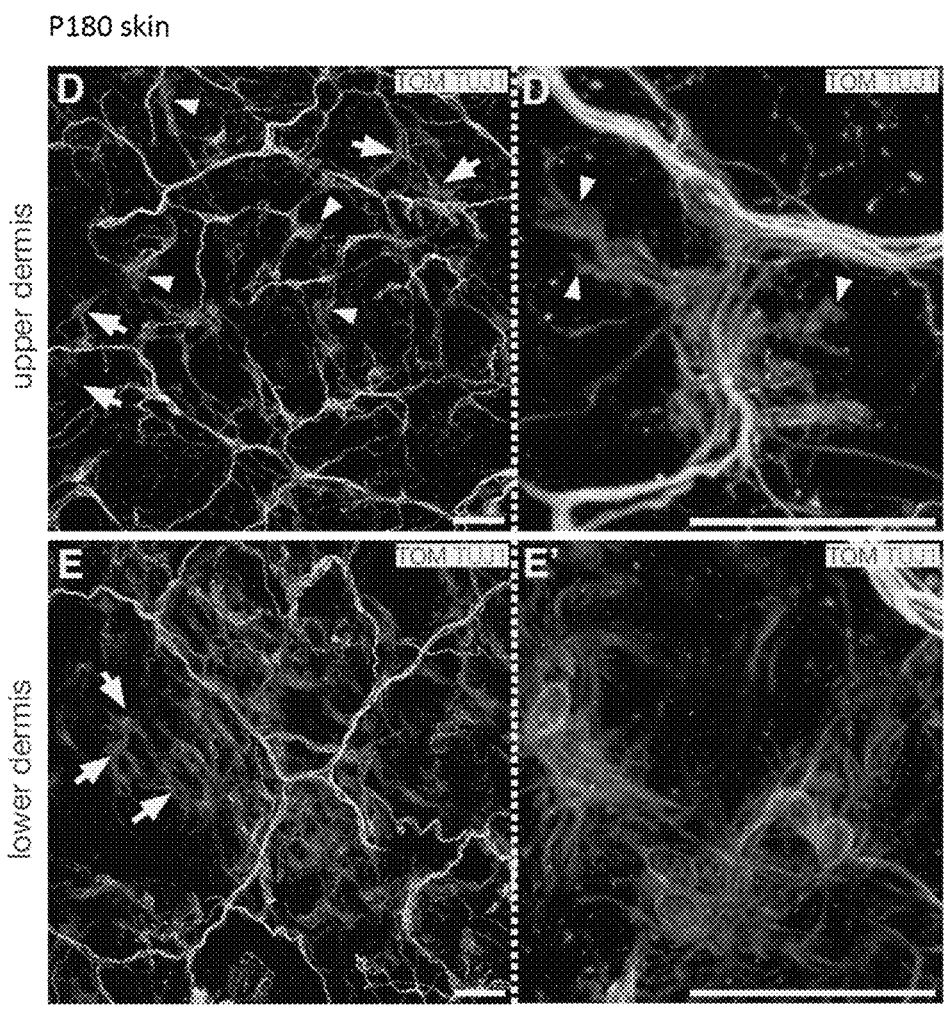
FIG. 10D-E'

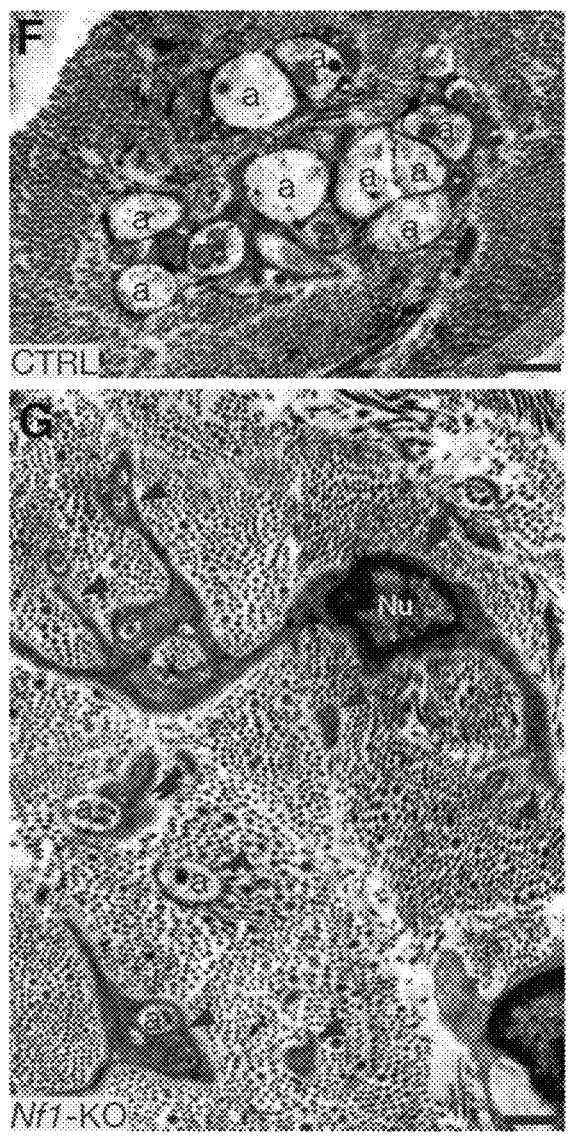
FIG. 10F-H

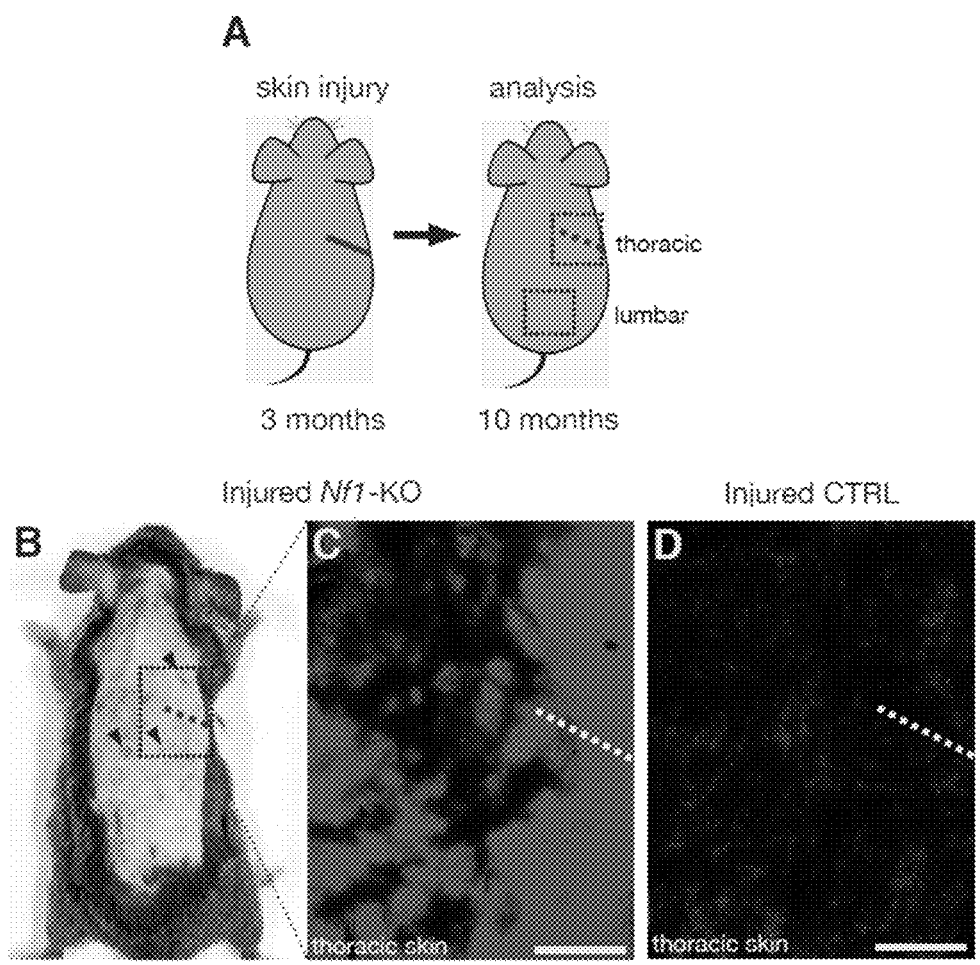
FIG. 11A-D

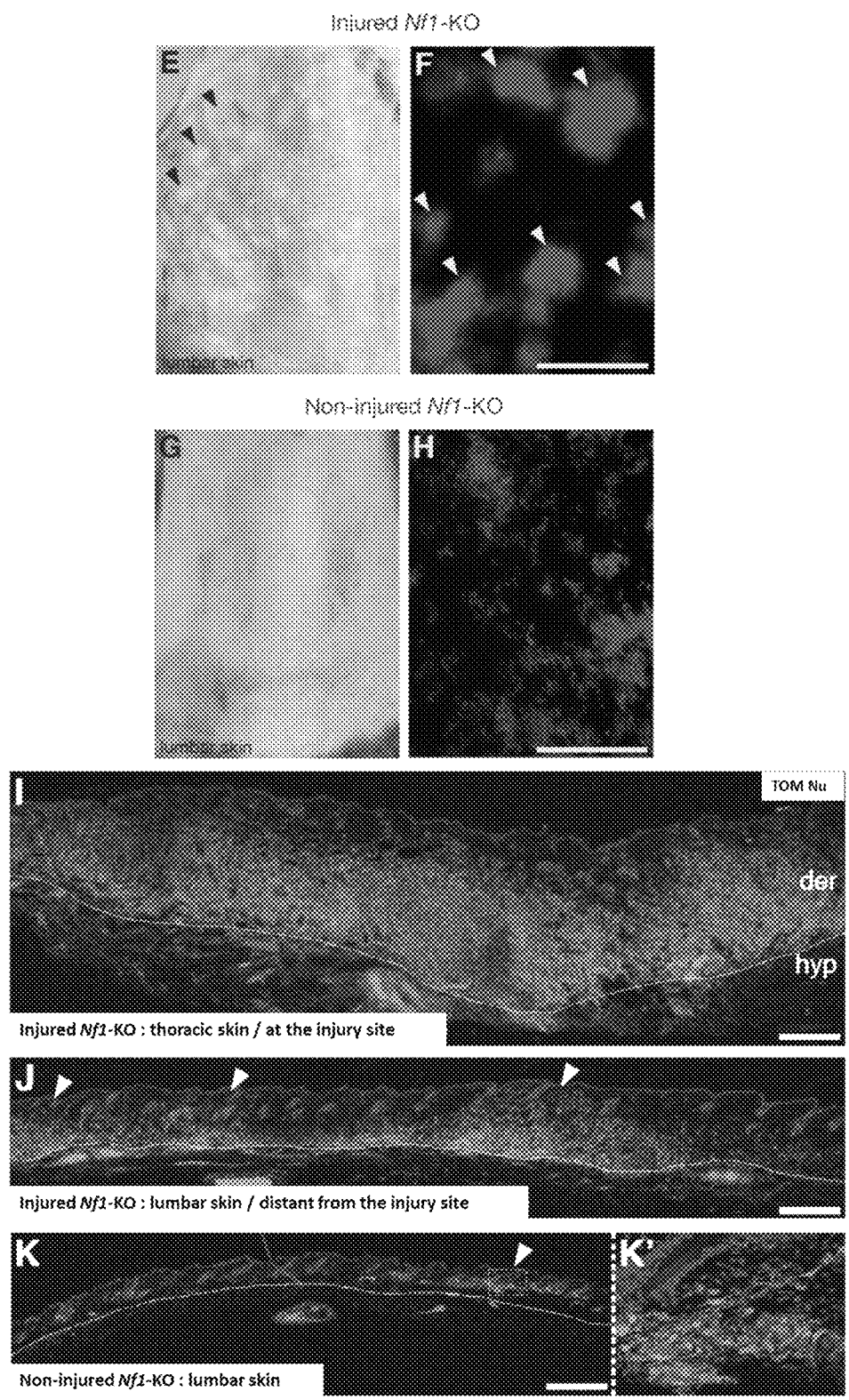
FIG. 11E-K'

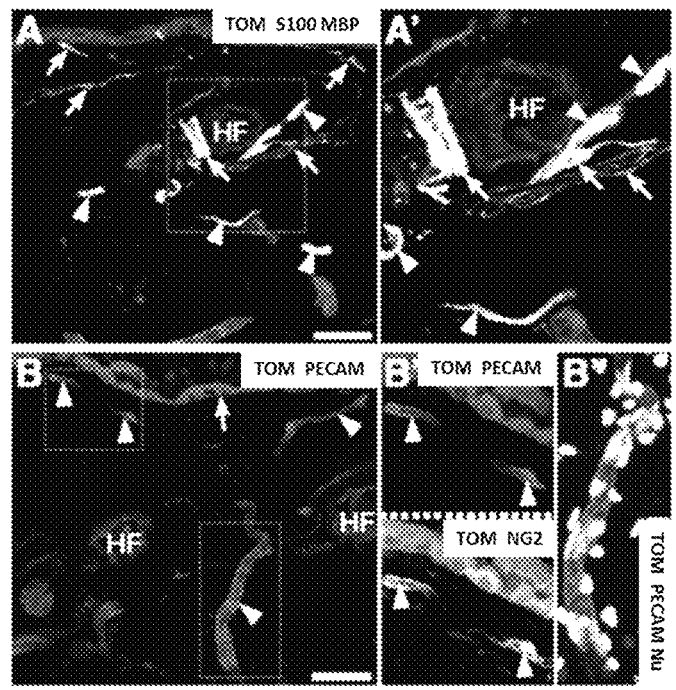
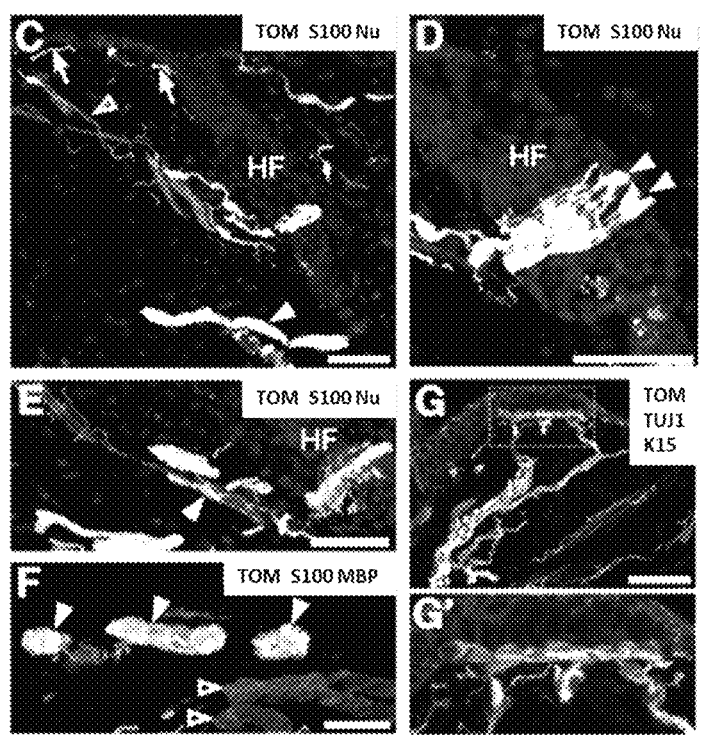
FIG. 12A-G'

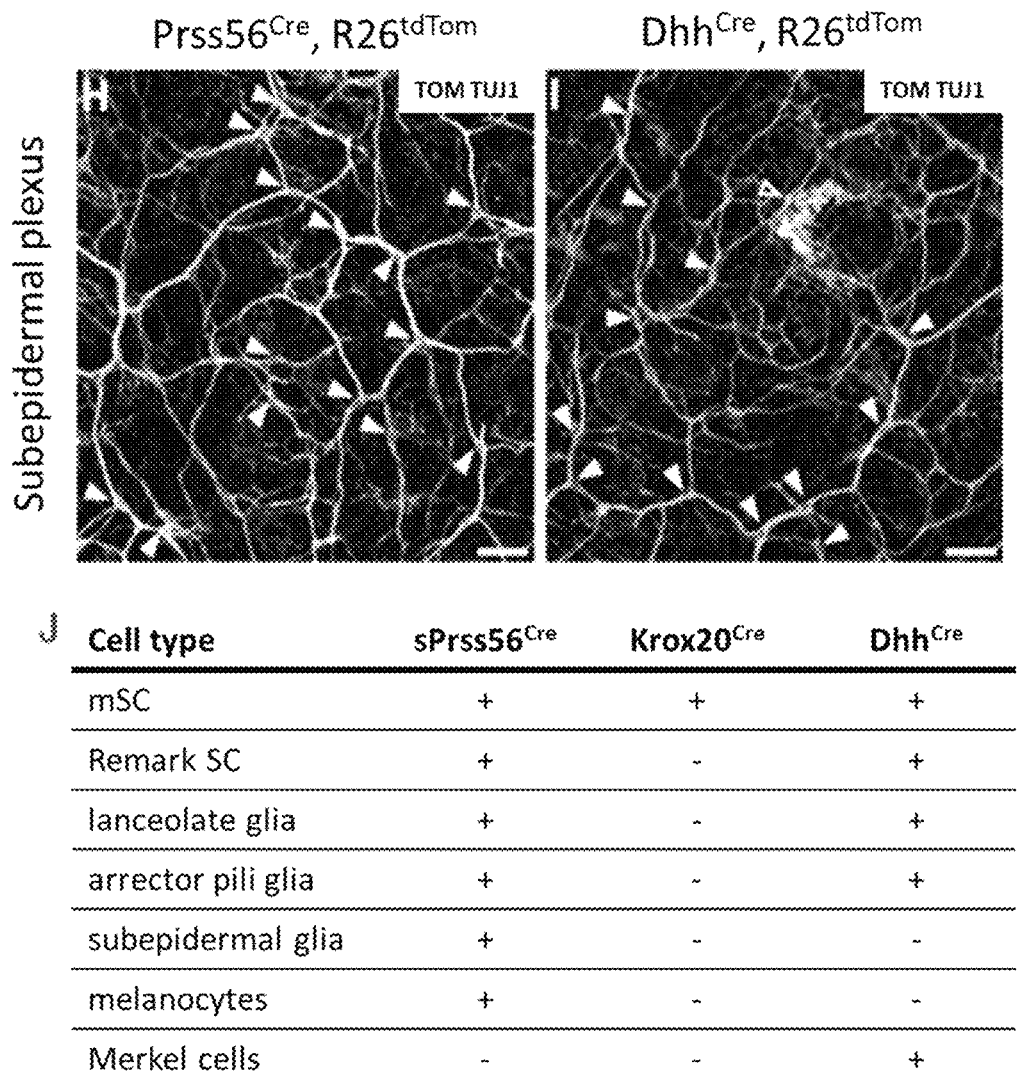
FIG. 12H-J

TRANSGENIC MOUSE MODEL OF NEUROFIBROMATOSIS TYPE 1

FIELD

The present invention relates to a non-human animal model of Neurofibromatosis type 1, and to the uses of this non-human animal model.

BACKGROUND

Neurofibromatosis type 1 is one of the most common genetic disorders, affecting 1 in 3000 individuals worldwide, and is caused by heterozygous inactivation of the tumour suppressor gene NF1 that predisposes patients to develop benign peripheral nerve tumours, termed neurofibromas (NFBs).

Virtually, all Neurofibromatosis type 1 patients develop cutaneous NFBs localised at the level of nerve terminals in the skin. Moreover, about 30% of the Neurofibromatosis type 1 patients develop plexiform tumours located along peripheral nerves with significantly higher incidence in cranial and spinal nerve roots (paraspinal NFB). In addition to cutaneous and plexiform NFBs, Neurofibromatosis type 1 patients are at increased risk of developing a variety of symptoms including optic nerve astrocytomas, Lisch nodules, hamartomas of the retina, cognitive dysfunctions (e.g., learning disability, lethargy and loss of attention), scoliosis, pseudarthrosis (in particular of long bones) and certain forms of myeloid leukaemia.

NFBs are composed of a mixture of Schwann cells (SCs) with other nerve fibre elements, such as axons, perineurial and endoneurial fibroblasts, blood vessels, mastocytes and macrophages. Although SCs have initially been considered as the primary pathogenic target, several recent studies suggest that NFBs arise as a result of NF1 loss at earlier stages in the SC lineage, possibly back to neural crest stem cells.

Currently, there is no effective treatment for this disease. The routinely used therapy involves surgical ablation of the NFBs. However, such interventions are often highly invasive and do not preclude the development of other NFBs. Indeed, several studies have suggested that the injury itself could be a factor that triggers the development of additional tumours.

During the past decade, considerable efforts have been devoted to set up genetically engineered mouse models for Neurofibromatosis type 1-associated NFBs (Gutmann D H, & Giovannini M. Neoplasia. 2002 July; 4(4): 279-290). Mice heterozygous for a constitutive mutation in the Nf1 gene are viable whereas homozygous die during embryonic development. Examples of available NF1 mouse models are the following: Nf1$^{+/-}$, neuronal Nf1 conditional knockout, melanocyte Nf1 conditional knockout, Schwann cell lineage Nf1 conditional knockout, Nf1 exon 23a knockout, Nf1$^{-/-}$ chimera and Nf1$^{+/-}$:p53$^{+/-}$.

These genetic tools have enabled major advances in the understanding of the mechanisms responsible for plexiform tumours formation and are used as models for drug screening studies. However, none of them recapitulates the development of diffuse cutaneous NFBs and other symptoms such as the CNS tumours, leukaemia, pseudarthrosis and scoliosis. Therefore, there is an urgent need to develop new animal models that faithfully recapitulate the different aspects of Neurofibromatosis type 1.

A neural crest-derived stem cell-like population has been observed in the embryo at the interface between the central and peripheral nervous systems. This embryonic, multipotent cell population is composed of cells which form the so-called boundary caps (BC). In the adult peripheral nervous system, BC cells give rise to Schwann cells, endoneurial fibroblasts and rare dermal stem cells, corresponding to BC derivatives (that may also be referred to as BC progeny) (Gresset et al., Stem Cell Reports. 2015 Aug. 11; 5(2):278-90).

A specific BC marker, Prss56, has recently been identified which encodes a trypsin-like serine protease (Gresset et al., Stem Cell Reports. 2015 Aug. 11; 5(2):278-90).

The inventors herein demonstrated that, surprisingly, inactivating the Nf1 gene specifically in Prss56-expressing cells (i.e., in particular, in the peripheral nervous system, in BC cells and derivatives thereof) leads to the development of both cutaneous and plexiform NFBs, but also to the development of marked splenomegaly, pseudarthrosis, hamartoma of the retina, spontaneous malignant transformation of neurofibromas and cognitive dysfunctions additional symptoms described in Neurofibromatosis type 1 patients. Therefore, this specific inactivation faithfully recapitulates the human Neurofibromatosis type 1 disease. This result was particularly surprising as other GEM models with cell specific inactivation of the Nf1, in particular in Krox20/Egr2 expressing cells, do not fully recapitulates the human NF1 disease. In particular, in this mouse model, no development of cutaneous NFB is observed.

The present invention thus relates to a non-human animal model of Neurofibromatosis type 1, wherein the Nf1 gene is specifically inactivated in Prss56-expressing cells and derivatives thereof, and to the use of said non-human animal model, for example in drug screening methods.

SUMMARY

The present invention relates to a transgenic non-human animal model for Neurofibromatosis type 1, wherein the Nf1 gene is specifically inactivated in Prss56-expressing cells and derivatives thereof.

In one embodiment, the Prss56-expressing cells and derivatives thereof are BC cells and derivatives thereof.

In one embodiment, BC cells derivatives are selected from the group consisting of non-myelinating Schwann cells, myelinating Schwann cells, endoneurial fibroblasts (characterised by the absence of basal lamina), melanocytes, dermal stem cells with neurogenic and gliogenic potential, satellite glial cells, nociceptive dorsal root ganglia (DRG) neurons, mechanoceptive DRG neurons and proprioceptive DRG neurons.

In one embodiment, the Nf1 gene is inactivated by complete or partial gene deletion. In a preferred embodiment, the Nf1 gene is inactivated by complete or partial gene deletion using the Cre-Lox recombination system.

In one embodiment, the genome of said model comprises:
  i) the Cre recombinase coding sequence under the control of a Prss56 promoter, preferably a genetic construct Prss56$^{Cre}$ in which the Cre recombinase coding sequence is inserted into the locus of Prss56, and
  ii) a floxed Nf1 gene.

In one embodiment, the transgenic non-human animal model according to the present invention comprises a biallelic Nf1 deletion in Prss56-expressing cells and derivatives thereof. In a preferred embodiment, the background of said model is Cre-inducible Nf1$^{fl/fl}$ or Cre-inducible Nf1$^{fl/-}$.

In one embodiment, the transgenic non-human animal model according to the present invention further comprises at least one reporter gene specifically expressed on Prss56-expressing cells and derivatives thereof.

In one embodiment, the genome of said model comprises:
i) the Cre recombinase coding sequence under the control of a Prss56 promoter, preferably a genetic construct Prss56$^{Cre}$ in which the Cre recombinase coding sequence is inserted into the locus of Prss56,
ii) a floxed Nf1 gene, and
iii) at least one Cre-activable reporter gene.

In one embodiment, the at least one reporter gene is selected from the group consisting of fluorescent proteins, preferably GFP, eGFP, DsRed, mCherry, tdTom, mStrawberry, mOrange, and mBanana and combinations thereof. In one embodiment, the at least one reporter gene is Cre-activable, preferably is R26R-GR or R26mT.

In one embodiment, the transgenic non-human animal model according to the present invention is a rodent. In a preferred embodiment, the transgenic non-human animal model according to the present invention is a mouse or a rat.

In one embodiment, the transgenic non-human animal model according to the present invention is for in vivo screening of a candidate compound, wherein said compound is for use as a drug for the treatment of Neurofibromatosis type 1, and wherein
i) the candidate compound is administered to said model, and
ii) the phenotype of said model is characterized after the administration of the candidate compound.

The present invention further relates to an in vitro method of producing cutaneous and plexiform NFBs and/or for studying the development and composition of cutaneous and plexiform NFB, comprising culturing in vitro Prss56-expressing cells and-derivatives thereof derived from tissues obtained from the transgenic non-human animal model according of the invention.

The present invention also relates to an in vitro method for screening a candidate compound, said compound being for use as a drug for treating cutaneous and/or plexiform NFBs, and said in vitro method comprising
i) culturing in vitro Prss56-expressing cells and-derivatives thereof derived from tissues obtained from the transgenic non-human animal model of the invention, and
ii) contacting said cells with the candidate compound.

BRIEF DESCRIPTION OF THE DRAWINGS

FIG. 9 represents Schwann cell hypertrophy and increased density of innervation in the 3-month old Nf1-KO dermis (A-D) Dorsal view of clarified 3-month-old skin from control (CTRL) (A, C) and Nf1-KO (B, D) animals immunolabelled for TOM and TUJ1. Abnormal morphology of Nf1-KO Schwann cells is apparent in the upper dermis (B), whereas mutant SCs in the lower dermis do not show obvious morphological atypia and are tightly associated with axons (D). Positions of the lanceolate nerve endings were used for anatomical orientation, and portions of the skin present above or below these structures were considered to be upper and lower dermis, respectively. Insets represent TOM labelling of the corresponding images. (E-G) Dorsal view of the clarified 3-month-old control (E) and Nf1-KO (F, G) upper dermis (containing or devoid of traced cells) immunolabelled for the pan-axonal marker TUJ1. The figures show maximum intensity projections of 35 μm thick z-stacks acquired from the skin surface. Insets represent TOM labelling of the corresponding images. (H) Quantification of TOM-positive sensory neurons in whole-mount preparations of control and Nf1-KO newborn DRGs at the cervical level. Each data point corresponds to the number of TOM-positive neurons per DRG. Data are represented as mean value +/−SD. Scale bar: 50 μm.

FIG. 10 represents 6-month-old Nf1-KO mutant skin contains numerous micro-cNFs. (A, B) Transverse sections through Nf1-KO mutant (A) and control (B) skin reveal local accumulations of TOM+ cells in the mutant dermis. The dotted lines indicate upper tissue limits and the boundaries between the dermis (der) and the hypodermis (hyp). (C) High magnification view of the mutant dermis shows abnormal morphology of TOM+/S100+ SCs. (D-E') Global (D, E) and higher magnification (D', E') views of the mutant skin in the upper and lower dermis showing aggregates of TOM+ SCs with abnormal morphologies. Most SCs extend abnormal cytoplasmic protrusions (arrowheads) or appear to be detached from the axons (arrows). (F, G) Electron micrographs showing typical non-myelinated nerve fibres in the control dermis (F) and a disrupted Remak bundle in a micro-cNF (G). Arrow indicates the perikaryon of a mutant SC devoid of axonal contact, and arrowheads indicate abnormal cytoplasmic extensions, often enwrapping pairs or single axons separated by collagenous extracellular matrix. a, axon ;. (H) Quantification of the relative abundance of different cell types in micro-cNFs and control skin. The data are represented as mean values measured per 0.026 μm2±SEM (*** p<0.0001). Fold change differences are given for each comparison. SC unit refers to SC soma or fragment of SC cytoplasm (>2 μm). Scale bar: 50 μm (A-E'), 1 μm (F, G).

FIG. 11 shows the skin injury promotes development of cNFs in Nf1-KO animals. (A) Experimental design. (B) Dorsal skin from a 10-month-old injured Nf1-KO mutant with multiple discrete skin (pale spots) and crusty lesions (arrowheads) all over the back skin. (C, D) Distribution of TOM+ cells in the thoracic skin of 10-month-old Nf1-KO mutant (C), and control (D) injured mice (dotted line indicates the site of lesion). (E-H) Lumbar skin from a 10-month-old injured Nf1-KO mouse (E, F) and an age-matched uninjured Nf1-KO mutant (G, H). Note in (E) the presence of numerous pale spots (arrowheads). (F, H) Higher magnification of the lumbar skin with direct TOM fluorescence. Arrowheads indicate aggregates of TOM+ cells, related to pale spots in E. (I-K') Transverse sections through thoracic (I) and lumbar (J) skin from the injured Nf1-KO animal and lumbar skin from the uninjured mutant (K). Dense accumulations of TOM+ cells are observed in the dermis, both at sites close to (I) and distant from (J, arrowheads) the injury. The skin from uninjured Nf1-KO contains only microscopic lesions, corresponding to micro-cNFs (arrowhead in K and magnified view in K'). Dotted line in I-K: boundary between dermis and hypodermis. Scale bar: 5 mm (C, D, F, H), 500 μm (I-K).

FIG. 12 represents the Tracing of the derivatives of Krox20+ and Dhh+ cells in the adult skin (A-B") Transverse sections of Krox20$^{Cre}$,R26$^{tdTom}$ skin stained with TOM and glial markers (A, A') and vascular markers, PECAM (endothelial cells, B-B") and NG2 (pericytes, B'). All traced S100+ SCs are MBP+ and therefore correspond to mSCs (arrowheads in A, A'). Note that S100+/MBP− nmSCs, including Remak SCs, lanceolate and subepidermal glia, are not traced (arrows in A, A'). TOM+ cells are also present in the epidermis (keratinocytes, arrow in B), inside the hair follicle (HF) and along capillaries (arrowheads in B). (C-G') Transverse sections of Dhh$^{Cre}$, R26$^{tdTom}$ skin stained for TOM, S100 (C-F), MBP (F), K15 (keratinocytes) and TUJ1 (axons) (G, G'). TOM+ cells correspond to a subset of Remak SCs (C, full arrowhead), lanceolate glia (D, arrowheads), mSCs (F, full arrowheads), Merkel cells of the touch dome (G, arrowhead), arrector pili glia together with arrector pili muscle (E, arrowhead, C, open arrowhead), and other muscle fibres (F, open arrowhead). No subepidermal glia are traced (C, arrows). (G') A higher magnification of the area indicated in (G). (H-I) Dorsal view of the subepidermal region from Prss56$^{Cre}$, R26$^{tdTom}$ (H) and Dhh$^{Cre}$, R26$^{tdTom}$ (I) adult skin. Note numerous TOM+ SCs associated with the subepidermal neuronal plexus (TUJ1-positive) in Prss56$^{Cre}$, R26$^{tdTom}$ dermis and absence of TOM labelling at this level with the Dhh$^{Cre}$ driver (arrowheads point to cell bodies of subepidermal SCs, empty arrowhead indicates Merkel cells). (J) Table summarising the type of derivatives in the adult skin traced with the three Cre drivers. Scale bar: 50 μm.

DETAILED DESCRIPTION

Figure 1:
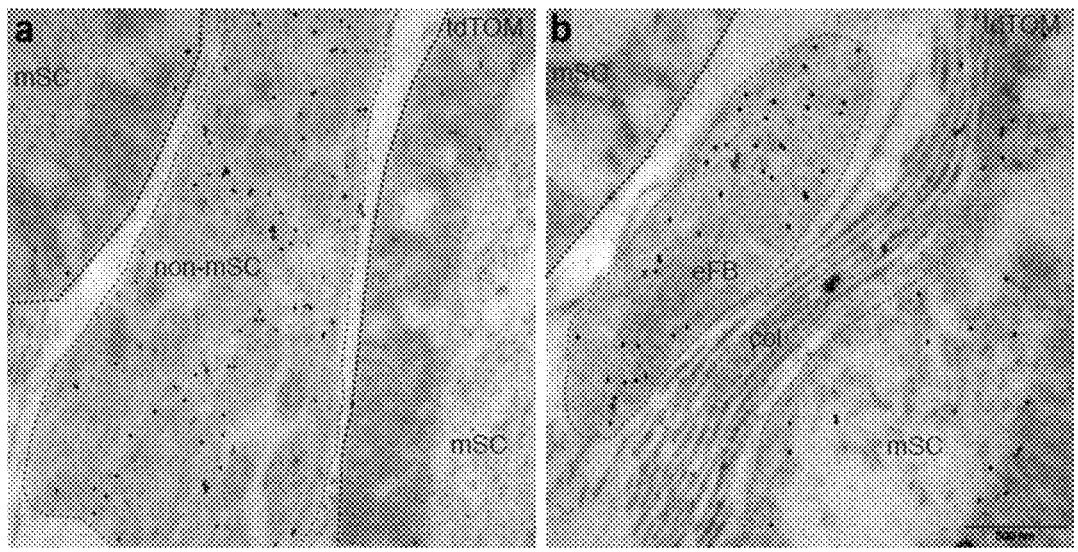
FIG. 1 is a set of electron microscopy ultrathin sections, showing the fate mapping of tdTom-expressing BC cell derivatives in adult nerve roots. tdTom-expressing cells (black dots in the dotted line area) correspond to a subset of non-myelinating (a; non-mSC) and myelinating (b; mSC) Schwann cells as well as endoneurial (b; eFB), but not the perineurial fibroblasts (not shown).

In the present invention, the following terms have the following meanings:

"Transgenic animal" refers to an animal having at least one non-endogenous (or heterologous) nucleic acid molecule stably integrated into its germline DNA (i.e., in the genomic sequence of some, most, or all of its cells). A heterologous nucleic acid molecule is introduced into the germ line of such transgenic mice by genetic manipulation of, for example, embryos or embryonic stem cells according to methods well known in the art. A "transgene" is meant to refer to such heterologous nucleic acid, such as a heterologous nucleic acid molecule in the form of an expression construct (such as for the production of a "knock-in" transgenic animal) or a heterologous nucleic acid molecule that upon insertion within or adjacent to a target gene results in a decrease in target gene expression (such as for production of a "knock-out" transgenic animal).

"Treating" or "treatment" refers to both therapeutic treatment and prophylactic or preventative measures; wherein the object is to prevent or slow down (lessen) Neurofibromatosis type 1. Those in need of treatment include those already with the disorder as well as those prone to have the disorder or those in whom the disorder is to be prevented. A subject or mammal is successfully "treated" for Neurofibromatosis type 1 if, after receiving a therapeutic amount of a compound, the subject shows observable and/or measurable relief to some extent of one or more of the symptoms associated with neurofibromatosis; reduced morbidity and mortality; or improvement in quality of life issues. In one embodiment, "treating" may refer to (1) delaying or preventing the onset of Neurofibromatosis type 1; (2) slowing down or stopping the progression, aggravation, or deterioration of one or more symptoms of Neurofibromatosis type 1 (such as, for example, cutaneous NFB (cNFB), plexiform NFB (pNFB), CNS tumours, myeloid leukaemia, malignant peripheral nerve sheath tumours, optic nerve glioma, optic nerve astrocytomas, Lisch nodules, hamartomas of the retina, cognitive dysfunctions (e.g., learning disability, lethargy and loss of attention), pseudarthrosis (in particular of long bone), scoliosis, splenomegaly, spontaneous malignant transformation of neurofibromas and the like); (3) bringing about ameliorations of the symptoms of Neurofibromatosis type 1; (4) reducing the severity or incidence of Neurofibromatosis type 1; or (5) curing Neurofibromatosis type 1.

DETAILED DESCRIPTION

The present invention relates to a transgenic non-human animal model for Neurofibromatosis type 1, wherein the Nf1 gene is specifically inactivated in Prss56-expressing cells and derivatives thereof (that may also be referred to as "progeny thereof").

In the peripheral nervous system, Prss56 is expressed only by boundary cap (BC) cells and derivatives thereof. Therefore, in one embodiment, said Prss56-expressing cell or derivative thereof is a boundary cap (BC) cell or a derivative thereof.

The non-human animal model disclosed in the present invention is the first animal model which has specific inactivation of the Nf1 gene in Prss56-expressing cells and derivatives thereof and exhibits major pathological symptoms of Neurofibromatosis type 1.

Prss56 (previously referred to as L20) encodes a protein named Serine protease 56 precursor (accession number: NP_081360.1 in *Mus musculus*). In mouse, the Prss56 gene (Gene ID: 69453) is present on chromosome 1 (NC_000067.6 (87183102..87188405)).

In the present invention, the Nf1 gene is specifically inactivated in Prss56-expressing cells and in derivatives thereof. As used herein, the term "a derivative of a Prss56-expressing cell" or "the progeny of a Prss56-expressing cell" (both term may be used interchangeably) refers to a cell obtained by growth, culture, division or differentiation (e.g., by in vivo differentiation or in vitro differentiation) of a cell having expressed at least once the Prss56 gene, i.e., wherein the mRNA of Prss56 or the Prss56 protein was produced at least once. In one embodiment, a derivative of a cell expressing Prss56 expresses Prss56. In another embodiment, a derivative of a cell expressing Prss56 does not express Prss56.

Examples of methods for determining if a cell expresses Prss56 are well known by the skilled artisan. As used herein, the term "expression" may refer alternatively or concomitantly to the transcription of the Prss56 gene (i.e., expression of the mRNA) or to the translation of Prss56 mRNA (i.e., expression of the protein). Methods for determining if a cell expresses Prss56 thus include, without limitation, determining the transcriptome (in an embodiment wherein expression relates to transcription of Prss56) or proteome (in an embodiment wherein expression relates to translation of Prss56) of the cell.

In one embodiment of the invention, the expression of Prss56 may be assessed at the RNA level. Methods for assessing the transcription level of Prss56 are well known in the prior art. Examples of such methods include, but are not limited to, RT-PCR, RT-qPCR, Northern Blot, hybridization techniques such as, for example, use of microarrays, and combination thereof including but not limited to, hybridization of amplicons obtained by RT-PCR, sequencing such as, for example, next-generation DNA sequencing (NGS) or RNA-seq (also known as "Whole Transcriptome Shotgun Sequencing") and the like.

Examples of PCR or qPCR primers that may be used for assessing the expression of Prss56 include, but are not limited to, the following couple of primers: SEQ ID NOs: 1-2, SEQ ID NOs: 3-4, SEQ ID NOs: 5-6 and SEQ ID NOs: 7-8.

```
SEQ ID NO: 1 (Forward primer):
5'-GTCACAATCCCCGAGAACAG-3'.

SEQ ID NO: 2 (Reverse primer):
5'-CTCGCTGAATAGCCGCTAAC-3'.

SEQ ID NO: 3 (Forward primer):
5'-GGTCTTCAGTGGCCTAGTGG-3'.

SEQ ID NO: 4 (Reverse primer):
5'-AGCCTCTGTCCTTGATCAGC-3'.

SEQ ID NO: 5 (Forward primer):
5'-CCTAGCGCTCCAACAGTGTC-3'.

SEQ ID NO: 6 (Reverse primer):
5'-AGTGCTCAGCTGGGATCTGT-3'.

SEQ ID NO: 7 (Forward primer):
5'-ATGACCTGGCCTTGGTACAG-3'.

SEQ ID NO: 8 (Reverse primer):
5'-GACAGGTGTCTGCACTGAGC-3'.
```

In one embodiment of the invention, the expression of Prss56 may be assessed at the protein level.

In vitro methods for determining a protein level in a sample are well-known in the art. Examples of such methods include, but are not limited to, immunohistochemistry, immunofluorescence, in situ hybridization Multiplex methods (Luminex), Western blot, enzyme-linked immunosorbent assay (ELISA), sandwich ELISA, fluorescent-linked immunosorbent assay (FLISA), enzyme immunoassay (EIA), radioimmunoassay (RIA), flow cytometry (FACS) and the like.

In vivo methods for determining a protein level are well-known in the art. Examples of such methods include, but are not limited to, computed tomography (CT scan), endoscopic ultrasound (EUS), magnetic resonance imaging (MRI), positron-emission tomography (PET), single photon emission tomography (SPECT), magnetic resonance cholangiopancreatography, fluorimetry, fluorescence, and near-infrared (NIR) fluorescent imaging.

In one embodiment, the Prss56-expressing cell or derivative thereof is a Krox20 expressing cell or a derivative thereof. In another embodiment, the Prss56-expressing cell does not derivate from a Krox20-expressing cell.

As used herein, "Krox20" refers to a transcription regulatory factor also known as Early growth response protein 2 (EGR2). In mouse, the Egr2 gene (Gene ID: 13654) is present on chromosome 10 (NC_000076.6 (67534453..67547493)).

In the peripheral nervous system, Prss56-expressing cells and derivatives thereof are BC cells and derivatives thereof (that may also be referred to as "progeny thereof"). Therefore, in one embodiment, in the peripheral nervous system of the non-human animal model of the invention, the Nf1 gene is specifically inactivated in BC cells and derivatives thereof.

Boundary cap (BC) cells are a neural crest-derived stem cell-like population identified in the embryo at the interface between the central nervous system and the peripheral nervous system. These cells form the so-called boundary caps which are transiently observed at the nerve root entry/exit points along the neural tube.

As used herein, the term "BC cell derivatives" or "BC cells progeny" (both terms may be used interchangeably) refers to cells obtained by differentiation (e.g., by in vivo differentiation or in vitro differentiation) of BC cells. Examples of BC cell derivatives in nerve roots include non-myelinating Schwann cells, myelinating Schwann cells, and endoneurial fibroblasts (characterised by the absence of basal lamina).

In the dorsal root ganglia, BC cell derivatives include satellite glial cells, nociceptive dorsal root ganglia (DRG) neurons, mechanoceptive DRG neurons and proprioceptive DRG neurons.

In the skin, BC cells derivatives include, but are not limited to non-myelinating Schwann cells, myelinating Schwann cells, endoneurial fibroblasts, melanocytes and dermal stem cells with neurogenic and gliogenic potential. Among these Schwann cells, some are associated with the dermal nerve fibers and others with nerve terminals, either lanceolate or free endings.

As used herein, the term "Nf1 gene" has its general meaning in the art and refers to the gene encoding the neurofibromin protein (NP_035027.1 in *Mus musculus*). In mouse, the Nf1 gene is located on the chromosome 11 (Gene ID: 18015, Position NC_000077.6 (79338389..79581609)).

As used herein, the expression "the Nf1 gene is specifically inactivated in Prss56-expressing cells and derivatives thereof" means that the inactivation of the Nf1 gene is present only in Prss56-expressing cells and derivatives thereof, while in other cell types, the Nf1 gene is functional and is equivalent to a wild-type Nf1 gene. In one embodiment, in the peripheral nervous system, the inactivation of the Nf1 gene is present only in BC cells and derivatives thereof, while in other cell types, the Nf1 gene is functional and is equivalent to a wild-type Nf1 gene.

In one embodiment, in other cell types than Prss56-expressing cells and derivatives thereof, one allele of the Nf1 gene is functional and equivalent to a wild-type Nf1 gene. In another embodiment, in other cell types than Prss56-expressing cells and derivatives thereof, both alleles of the Nf1 gene are functional and equivalent to a wild-type Nf1 gene.

In one embodiment, the inactivation of Nf1 in Prss56-expressing cells and derivatives thereof is monoallelic. By "monoallelic" is meant that one allele of the Nf1 gene only is inactivated in Prss56-expressing cells and derivatives thereof, while the other allele is functional and equivalent to a wild-type Nf1 gene (denoted Nf1$^{-/+}$ in the non-human animal model).

In another embodiment, the inactivation of Nf1 in Prss56-expressing cells and derivatives thereof is biallelic. By "biallelic" is meant that both alleles of the Nf1 gene are inactivated in Prss56-expressing cells and derivatives thereof (denoted Nf1$^{-/-}$ in the non-human animal model).

As used herein, the term "inactivated" refers to the interruption or to the suppression of the expression of a gene at the transcriptional and/or translational level, or to the expression of a truncated protein or of a mutated protein such that it cannot perform its function.

In one embodiment, the inactivation of a gene is due to a mutation of the gene. In the meaning of the present invention, the term "mutation" refers to a stable change in the genetic sequence. Examples of mutations which could lead to the inactivation of a gene in the present invention include, but are not limited to, point mutations, insertions, deletions and amplification.

Preferably, the mutation is a deletion. The term "deletion" as used herein means the loss or absence of a part (partial gene deletion) or of the complete sequence (complete gene deletion) of a gene.

In one embodiment, the deletion starts at or before the start codon of the deleted gene, and ends at or after the stop codon of the deleted gene (i.e., complete gene deletion).

In another embodiment, only a part of the gene sequence is deleted (i.e., the deletion is a partial gene deletion), for example one or more exons are deleted, thus resulting in a loss of function of the encoded protein. In one embodiment, the inactivation of the Nf1 gene results from the deletion of at least 1, 2, 3, 4, 5 or more exons. In one embodiment, the inactivation of the Nf1 gene results from the deletion of at least exon 31, 32 and/or 23. In one embodiment, the inactivation of the Nf1 gene results from the deletion of at least exons 31 and 32. In one embodiment, the inactivation of the Nf1 gene results from the deletion of at least exon 23.

Systems for inducing the inactivation of genes in specific cells or tissues are known in the art, and include, without limitation, recombination systems such as, for example, the Cre-Lox system, the FLP-FRT system, the φC31 bacteriophage-mediated recombination system, the DRE-rox system and the like.

In one embodiment, the specific inactivation of the Nf1 gene in Prss56-expressing cells and derivatives thereof is obtained using the Cre-Lox system.

The Cre recombinase (Cre) is a member of the integrase family of recombinases from the P1 bacteriophage that catalyses site-specific recombination of DNA between loxP recognition sites.

As used herein, the term "Cre recombinase" or "Cre" is meant to encompass wild-type, P1 bacteriophage-derived Cre enzyme (NCBI Reference Sequence: YP_006472.1) with amino acid sequence SEQ ID NO: 9 (encoded by cDNA nucleic acid sequence SEQ ID NO: 10) and mutants thereof. Mutants of the Cre recombinase are well-known in the art, and include, without limitation, improved Cre (iCre; Shimshek et al., Genesis. 2002 January; 32(1):19-26), R32V, R32M and 303GVSdup (Eroshenko N & Church G M, Nat Commun. 2013; 4:2509). In one embodiment, a mutant of Cre recombinase is an enzyme having at least 75, 80, 85, 90, 95, 96, 97, 98, 99% or more sequence identity with SEQ ID NO: 9 and having the same recombinase activity than the Cre enzyme with amino acid sequence SEQ ID NO: 9.

SEQ ID NO: 9

MSNLLTVHQNLPALPVDATSDEVRKNLMDMFRDRQAFSEHTWKMLLSVCR

SWAAWCKLNNRKWFPAEPEDVRDYLLYLQARGLAVKTIQQHLGQLNMLHR

RSGLPRPSDSNAVSLVMRRIRKENVDAGERAKQALAFERTDFDQVRSLME

NSDRCQDIRNLAFLGIAYNTLLRIAEIARIRVKDISRTDGGRMLIHIGRT

KTLVSTAGVEKALSLGVTKLVERWISVSGVADDPNNYLFCRVRKNGVAAP

SATSQLSTRALEGIFEATHRLIYGAKDDSGQRYLAWSGHSARVGAARDMA

RAGVSIPEIMQAGGWTNVNIVMNYIRNLDSETGAMVRLLEDGD..

Within the meaning of the present invention, the term "identity", when it is used in a relationship between the sequences of two or more amino acid sequences, refers to the degree of relationship between these amino acid sequences, as determined by the number of correspondences between strings of two or more amino acid residues.

According to the invention, "identity" corresponds to a percentage of identity between two sequences or more. This percentage is defined as a number of positions for which the amino acids are identical when the sequences are aligned optimally, divided by the total number of amino acids. The differences between the sequences may be distributed at random and over all their lengths.

Two sequences are said to be aligned optimally when the percentage of identity is maximal. Moreover, as will be clear to a person skilled in the art, it may be necessary to have recourse to additions of gaps so as to obtain an optimum alignment between the two sequences. The percentage of identity between two amino acids sequences can therefore be determined by comparing these two sequences aligned optimally in which the amino acids sequence to be compared may comprise additions or deletions compared with the reference sequence for optimum alignment between these two sequences. The percentage of identity is then calculated by determining the number of identical positions for which the amino acid is identical between the two sequences, dividing this number of identical positions by the total number of positions in the comparison window and multiplying the result obtained by 100 in order to obtain the percentage identity between these two sequences.

Preferably, the methods for determining identity are designed to give the greatest possible agreement between the compared sequences.

The percentage identity can be determined by a particular mathematical model or by a computer program (generally designated by the term "algorithm"). Methods for calculating the identity between nucleotide sequences are well known to persons skilled in the art. Non-limitative examples of such methods include those described in the following documents: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math., 48, 1073 (1988).

Methods for determining identity have been described in computer programs accessible to the public. Preferred examples of methods using computer programs include, without being limited thereto, the GCG software, including GAP (Devereux et al., Nucl. Acid. Res.\2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is available from the National Center for Biotechnology Information (NCBI) and other sources (BLAST Manual, Altschul et al., NCB/NLM/NIH Bethesda, Md. 20894; Altschul et al., J. Mol. Biol. 215, 403-410 (1990)). The Smith-Waterman algorithm, which is well known to persons skilled in the art, can also be used to determine the percentage identity between two sequences.

loxP is a 34-bp sequence derived from the P1 bacteriophage, comprising a central and variable 8-bp sequence between two sets of 13-bp inverted repeat sequences. Wild-type loxP sequence (i.e., loxP sequence from the P1 bacteriophage) comprises the nucleic acid sequence ATAACTTCGTATANNNTANNNTATACGAAGTTAT (SEQ ID NO: 11), with N being any of A, T, C, or G. In one embodiment, the wild-type loxP used in the present invention comprises the nucleic acid sequence (5'-ATAACTTCGTATAATGTATGCTATACGAAGTTAT-3', SEQ ID NO: 12). However, alternate loxP sites have been described in the art and may be used in the present invention. Examples of alternative loxP sites include, without limitation, lox511, lox5171, lox2272, loxLE, lox71, lox66, loxP from M2 bacteriophage, loxP from M3 bacteriophage, loxP from M7 bacteriophage and loxP from M11 bacteriophage, which sequences are well-known from the skilled artisan.

Recombination products depend on the number and orientation of the loxP sites. If two loxP sites are located on different DNA molecules (for example, in trans), translocation between the two molecules (for example, chromosomes) will occur. In other examples, DNA between two loxP sites in the same orientation will be excised and DNA between loxP sites in opposite orientations will be inverted with respect to its starting orientation. See, e.g., Nagy A, Genesis. 2000 February; 26(2):99-109.

In one embodiment, the transgenic non-human animal model of the invention expresses the Cre recombinase under the control of a Prss56 promoter and comprises a floxed Nf1 gene. By "floxed Nf1 gene" is meant a Nf1 gene which is flanked by loxP sites on each end, or which comprises two loxP sites. Consequently, in Prss56-expressing cells, recombination between the two loxP recognition sites results in the deletion of a part or of the complete sequence of the Nf1 gene. Said deletion of a part or of the complete sequence of the Nf1 gene is therefore present in the progeny of Prss56-expressing cells.

In one embodiment, the transgenic non-human animal model comprises i) a genetic construct $Prss56^{Cre}$, in which the Cre recombinase coding sequence is inserted into the locus of Prss56 thereby resulting in the expression of the Cre recombinase under the control of the Prss56 promoter, and ii) a floxed Nf1 gene.

In one embodiment, the non-human animal model of the invention comprises the $Prss56^{Cre}$ knock-in allele described in Gresset et al., (Stem Cell Reports. 2015 Aug. 11; 5(2): 278-90). Briefly, the Cre coding sequence is inserted at the level of Prss56 initiation ATG codon. Insertion of the $Prss56^{Cre}$ knock-in allele in the genome of the non-human animal model may be verified by PCR, using the following primers: forward primer: 5'-CAGGTGAGGTGCGGAC-CATT-3' (SEQ ID NO: 13), reverse primer: 5'-ACG-GAAATCCATCGCTCGACCAGTT-3' (SEQ ID NO: 14).

In one embodiment, the non-human animal model of the invention comprises a floxed Nf1 gene, with loxP sites flanking exons 31 and 32 of the Nf1 gene. According to this embodiment, recombination between the two loxP sites results in the deletion of at least exons 31 and 32.

In another embodiment, both alleles of the Nf1 gene of the non-human animal model of the invention are floxed, and the background of the non-human animal model is thus $Nf1^{fl/fl}$. Preferably, the background of the non-human animal model is Cre-inducible $Nf1^{fl/fl}$.

In one embodiment, only one allele of the Nf1 gene of the non-human animal model of the invention is floxed.

In a first embodiment, one allele of the Nf1 gene of the non-human animal model of the invention is floxed and the second allele of the Nf1 gene is inactivated in a non-specific manner, i.e., is inactivated in all cells of the non-human transgenic model of the invention. The background of the non-human animal model is thus $Nf1^{fl/-}$. Preferably, the background of the non-human animal model is Cre-inducible $Nf1^{fl/-}$.

Examples of methods for inactivating the second allele of Nf1 include, but are not limited to, complete or partial deletion of the sequence of the Nf1 gene (such as, for example, deletion of exons 31 and 32, deletion of exon 23), non-sense mutation, insertion of a premature stop codon and the like.

In a second embodiment, one allele of the Nf1 gene of the non-human animal model of the invention is floxed and the second allele of the Nf1 gene is wild-type. The background of the non-human animal model is thus Nf1$^{fl/+}$. Preferably, the background of the non-human animal model is Cre-inducible Nf1$^{fl/+}$.

In one embodiment, the transgenic non-human animal model further comprises at least one reporter gene specifically expressed in Prss56-expressing cells and derivatives thereof. As used herein, the expression "reporter gene specifically expressed in Prss56-expressing cells and derivatives thereof" means that the reporter gene is expressed only in Prss56-expressing cells and derivatives thereof but not in other cell types. In one embodiment, in the peripheral nervous system, the at least one reporter gene is specifically expressed in BC cells and derivatives thereof.

In one embodiment, the expression of said reporter gene leads to detectable signals such as, without limitation, enzymatic non-fluorescent, fluorescent or bioluminescent emissions.

In one embodiment, the transgenic non-human animal model of the invention expresses the Cre recombinase under the control of a Prss56 promoter and expresses at least one Cre-activable reporter gene.

In one embodiment, the genome of the transgenic non-human animal model comprises i) a genetic construct Prss56$^{Cre}$ in which the Cre recombinase coding sequence is inserted into the locus of Prss56 (thereby resulting in the expression of the Cre recombinase under the control of the Prss56 promoter), ii) a floxed Nf1 gene and iii) at least one Cre-activable reporter gene.

In another embodiment, the transgenic non-human animal model of the invention expresses at least one reporter gene under the control of a Prss56 promoter.

In one embodiment, the reporter gene is selected from the group comprising genes encoding fluorescent proteins.

As used herein, the term "fluorescent protein" refers to a protein that emits fluorescence of a particular wavelength (color) when excited by a different wavelength of light. Green fluorescent protein (GFP) was the first identified member of this family. GFPs are derived from marine organisms such as *Aequorea victoria* and *Renilla reniformis*, and emit green fluorescence when exposed to blue light. GFP includes both wild type GFP and derivatives of GFP, such as GFP with one or more mutations that improve characteristics of fluorescence, photostability or folding of the protein (for example, enhanced GFP (EGFP); see, e.g., U.S. Pat. No. 6,172,188). Additional mutations in GFPs produce fluorescent proteins with different coloured emissions. These include blue fluorescent proteins, cyan fluorescent proteins, yellow fluorescent proteins and red fluorescent proteins (RFP), such as the tetrameric DsRed. RFPs also include variants of DsRed, such as variants that form monomers or dimers, or have altered emission spectra (ranging from yellow to red) tdTom, mCherry, mStrawberry, mOrange, and mBanana.

In one embodiment, the reporter gene encodes a protein selected from GFP, eGFP, DsRed, mCherry, tdTom, mStrawberry, mOrange and mBanana and combinations thereof.

In one embodiment, the reporter gene is Cre-activable. Examples of Cre-activable reporter genes include, but are not limited to, R26R-GR, and R26tdTom.

In one embodiment, the reporter gene is selected from the group comprising genes encoding enzymatic non-fluorescent proteins. Examples of enzymatic non-fluorescent reporter proteins include, but are not limited to, β-galactosidase, alkaline phosphatase and peroxidase.

In one embodiment, the non-human animal is a mammal, such as, for example, a rodent (preferably a mouse or a rat), a rabbit, a pig or a non-human primate.

In one embodiment, the non-human animal is a mouse. Any genetic background of mouse may be used in the present invention. Examples of genetic backgrounds of mice include, but are not limited to, C57BL/6, DBA2, FVB/N, NOD, BALB/c, C3H, B6D2F1 and crosses thereof.

In one embodiment, the non-human animal is Prss56$^{Cre/+}$:R26$^{tdTom/+}$:Nf1$^{fl/+}$. In one embodiment, the non-human animal is Prss56$^{Cre/+}$:R26$^{R-GR/+}$:Nf1$^{fl/+}$. In one embodiment, the non-human animal is Prss56$^{Cre/+}$:R26$^{tdTom/+}$:Nf1$^{fl/fl}$. In one embodiment, the non-human animal is Prss56$^{Cre/+}$:R26$^{tdTom/+}$:Nf1$^{fl/-}$. In one embodiment, the non-human animal is Prss56$^{Cre/+}$:R26$^{R-GR/+}$:Nf1$^{fl/fl}$. In one embodiment, the non-human animal is Prss56$^{Cre/+}$:R26$^{R-GR/+}$:Nf1$^{fl/-}$.

The present invention further relates to a method for generating a transgenic non-human animal model for Neurofibromatosis type 1, wherein the Nf1 gene is specifically inactivated in Prss56-expressing cells and derivatives thereof.

Transgenic non-human animals of the invention may be produced by methods well known in the art. There are a number of techniques that allow the introduction of genetic material, such as a transgene, into the germline. The most commonly used, and preferred protocol comprises direct injection of the transgene into the male pronucleus of the fertilised egg, resulting in the random integration into one locus of a varying number of copies, usually in a head to tail array. The injected eggs are then re-transferred into the uteri of pseudo-pregnant recipient mothers. Some of the resulting offspring may have one or several copies of the transgene integrated into their genomes, usually in one integration site. These "founder" animals are then bred to establish transgenic lines and to back-cross into the genetic background of choice.

As used herein, the term "founder animal" refers to an animal which allows next generation progenies and those coming after to survive as maintaining a desired phenotype.

In one embodiment, founder animals include, but are not limited to, wild-type, Nf1$^{fl/fl}$, Nf1$^{fl/-}$, Nf1$^{fl/+}$, Nf1$^{+/-}$, Prss56$^{Cre}$, R26$^{R-GR}$ and R26$^{tdTom}$ and combinations thereof. In one embodiment, founder animals include, but are not limited to, wild-type, Nf1$^{fl/fl}$, Nf1$^{fl/-}$, Nf1$^{fl/+}$, Nf1$^{+/-}$, Prss56$^{Cre}$:R26$^{R-GR}$ and Prss56$^{Cre}$:R26$^{tdTom}$.

In one embodiment, founder animals are bred to obtain a F1 generation. In one embodiment, founder animals are bred in a Nf1$^{fl/fl}$ background. In one embodiment, founder animals are bred in a Nf1$^{fl/-}$ background. In one embodiment, founder animals are bred in a Nf1$^{fl/+}$ background. In one embodiment, founder animals are bred in a Nf1$^{+/-}$ background.

In one embodiment, Prss56$^{Cre}$/R26$^{tdTom}$ animals are bred onto a Nf1$^{fl/fl}$ background. Accordingly, the F1 generation is Prss56$^{Cre/+}$:R26$^{tdTom/+}$:Nf1$^{fl/+}$.

In one embodiment, Prss56$^{Cre}$/R26$^{R-GR}$ animals are bred onto a Nf1$^{fl/fl}$ background. Accordingly, the F1 generation is Prss56$^{Cre/+}$:R26$^{R-GR/+}$:Nf1$^{fl/+}$.

In one embodiment, F1 generation animals are bred to obtain a F2 generation.

In one embodiment, Prss56$^{Cre/+}$:R26$^{tdTom/+}$:Nf1$^{fl/+}$ are bred onto a Nf1$^{fl/fl}$ background. Accordingly, the F2 generation is Prss56$^{Cre/+}$:R26$^{tdTom/+}$:Nf1$^{fl/fl}$.

In one embodiment, Prss56$^{Cre/+}$:R26$^{tdTom/+}$:Nf1$^{fl/+}$ are bred onto a Nf1$^{fl/-}$ background. Accordingly, the F2 generation is Prss56$^{Cre/+}$:R26$^{tdTom/+}$:Nf1$^{fl/-}$.

In one embodiment, Prss56$^{Cre/+}$:R26$^{R-GR}$/+:Nf1$^{fl/+}$ are bred onto a Nf1$^{fl/fl}$ background. Accordingly, the F2 generation is Prss56$^{Cre/+}$:R26$^{R-GR/+}$:Nf1$^{fl/fl}$.

In one embodiment, Prss56$^{Cre/+}$:R26$^{R-GR/+}$:Nf1$^{fl/+}$ are bred onto a Nf1$^{fl/-}$ background. Accordingly, the F2 generation is Prss56$^{Cre/+}$:R26$^{R-GR/+}$:Nf1$^{fl/-}$.

Alternatively, for the production of transgenic mice, transgenes can be introduced via embryonic stem (ES) cells, using electroporation, retroviral vectors or lipofection for gene transfer. This is followed by the random insertion into the genome of the pluripotent embryonic stem (ES) cells, followed by the production of chimeric mice and subsequent germline transmission.

The transgenic animals can be subsequently tested to ensure the required genotypic change has been effected, in any suitable fashion. This can be done by, for example, detecting the presence of the transgene by PCR with specific primers, or by Southern blotting of tail DNA with a specific probe. Testing for homologous recombination leading to insertion of the transgene may be done by restriction digestion. The band sizes seen if recombination has taken place are different to those seen if it has not. Testing for homozygosity of the transgene insertion may be carried out using quantitative Southern blotting to detect a two-fold difference in signal strength between hetero-and homozygous transgenic animals. Confirmation that the gene is not being expressed can be carried out by immunohistochemical techniques.

The present invention further relates to the use of the transgenic non-human animal model of the invention in an in vivo method for screening a candidate compound for treating Neurofibromatosis type 1 comprising i) administering said model with the candidate compound ii) characterizing the phenotype of said model after the administration of the candidate compound and iii) positively selecting the candidate compound that prevents, reduces, reverses or delays the phenotype of said transgenic non-human animal model as compared to the control.

The present invention further relates to an in vivo method for screening a candidate compound for treating Neurofibromatosis type 1 comprising i) administering said model with the candidate compound ii) characterizing the phenotype of said model after the administration of the candidate compound and iii) positively selecting the candidate compound that prevents, reduces, reverses or delays the phenotype of said transgenic non-human animal model as compared to the control.

Examples of physiological or pathological changes that may be assessed in the method of the invention, or of phenotype that may be characterised include, without limitation: presence and/or development of cutaneous NFB (cNFB), presence and/or development of plexiform NFB (pNFB), presence and/or development of CNS tumours, presence and/or development of myeloid leukaemia, presence and/or development of malignant peripheral nerve sheath tumours, presence and/or development of optic nerve glioma, optic nerve astrocytomas, Lisch nodules and hamartoma of the retina, presence and/or evolution of cognitive dysfunction (e.g., of learning disability, lethargy and loss of attention), presence and/or development of pseudarthrosis (in particular of long bones), presence and/or development of scoliosis, presence and/or development of splenomegaly, spontaneous malignant transformation of neurofibromas and the like.

In one embodiment, the physiological or pathological changes that is assessed in the method of the invention, or the phenotype that is characterised is selected from the presence and/or development of cutaneous NFB (cNFB), presence and/or development of plexiform NFB (pNFB), presence and/or development of CNS tumours, presence and/or development of myeloid leukaemia, presence and/or development of malignant peripheral nerve sheath tumours, Lisch nodules and hamartoma of the retina, presence and/or evolution of cognitive dysfunction (e.g., of learning disability, lethargy and loss of attention), presence and/or development of pseudarthrosis (in particular of long bones), presence and/or development of splenomegaly, spontaneous malignant transformation of neurofibromas and the like.

The present invention further relates to an in vivo method for screening a candidate compound for treating cutaneous NFB (cNFB) comprising i) administering said model with the candidate compound ii) characterizing the phenotype of said model after the administration of the candidate compound and iii) positively selecting the candidate compound that prevents, reduces, reverses or delays cNFB in said transgenic non-human animal model as compared to the control.

The present invention further relates to an in vivo method for screening a candidate compound for treating plexiform NFB (pNFB) comprising i) administering said model with the candidate compound ii) characterizing the phenotype of said model after the administration of the candidate compound and iii) positively selecting the candidate compound that prevents, reduces, reverses or delays pNFB in said transgenic non-human animal model as compared to the control.

The present invention further relates to an in vivo method for screening a candidate compound for treating Myeloid leukaemia comprising i) administering said model with the candidate compound ii) characterizing the phenotype of said model after the administration of the candidate compound and iii) positively selecting the candidate compound that prevents, reduces, reverses or delays myeloid leukaemia in said transgenic non-human animal model as compared to the control.

The present invention further relates to an in vivo method for screening a candidate compound for treating malignant peripheral nerve sheath tumours comprising i) administering said model with the candidate compound ii) characterizing the phenotype of said model after the administration of the candidate compound and iii) positively selecting the candidate compound that prevents, reduces, reverses or delays malignant peripheral nerve sheath tumours in said transgenic non-human animal model as compared to the control.

The present invention further relates to an in vivo method for screening a candidate compound for treating Lisch nodules and/or hamartoma of the retina comprising i) administering said model with the candidate compound ii) characterizing the phenotype of said model after the administration of the candidate compound and iii) positively selecting the candidate compound that prevents, reduces, reverses or delays Lisch nodules and/or hamartoma of the retina in said transgenic non-human animal model as compared to the control.

The present invention further relates to an in vivo method for screening a candidate compound for treating cognitive dysfunction (e.g., of learning disability, lethargy and loss of attention) comprising i) administering said model with the candidate compound ii) characterizing the phenotype of said model after the administration of the candidate compound and iii) positively selecting the candidate compound that prevents, reduces, reverses or delays cognitive dysfunction in said transgenic non-human animal model as compared to the control.

The present invention further relates to an in vivo method for screening a candidate compound for treating pseudarthrosis (in particular of long bones) comprising i) administering said model with the candidate compound ii) characterizing the phenotype of said model after the administration of the candidate compound and iii) positively selecting the candidate compound that prevents, reduces, reverses or delays pseudarthrosis in said transgenic non-human animal model as compared to the control.

The present invention further relates to an in vivo method for screening a candidate compound for treating splenomegaly comprising i) administering said model with the candidate compound ii) characterizing the phenotype of said model after the administration of the candidate compound and iii) positively selecting the candidate compound that prevents, reduces, reverses or delays splenomegaly said transgenic non-human animal model as compared to the control.

The present invention further relates to an in vivo method for screening a candidate compound for treating spontaneous malignant transformation of neurofibromas comprising i) administering said model with the candidate compound ii) characterizing the phenotype of said model after the administration of the candidate compound and iii) positively selecting the candidate compound that prevents, reduces, reverses or delays spontaneous malignant transformation of neurofibromas said transgenic non-human animal model as compared to the control.

In one embodiment, the control is a transgenic non-human animal of the invention that did not received the compound. In one embodiment, the control is a transgenic non-human animal of the invention, such as, for example, $Prss56^{Cre/+}$: $R26^{tdTom/+}$:$Nf1^{fl/+}$ and/or $Prss56^{Cre/+}$:$R26^{R-GR/+}$:$Nf1^{fl/+}$ and having or not received the compound.

In one embodiment, the in vivo screening method of the invention comprises comparing physiological and pathological changes of a transgenic non-human animal as described hereinabove having received the compound with a transgenic non-human animal as described hereinabove that did not received the compound and/or with a transgenic non-human animal as described hereinabove and having or not received the compound.

Candidate compounds positively selected in the screening methods of the invention may be used to prevent or treat Neurofibromatosis type 1, cNFB, pNFB, myeloid leukaemia, malignant peripheral nerve sheath tumours, Lisch nodules and/or hamartoma of the retina, cognitive dysfunction, pseudarthrosis, splenomegaly, or spontaneous malignant transformation of neurofibromas respectively. Accordingly, the condition of a patient suffering from such a disease can be improved by administration of such a product. The formulation of the product for use in preventing or treating the disease will depend upon factors such as the nature of the agent identified, the precise combination of symptoms, and the severity of the disease. Typically, the agent is formulated for use with a pharmaceutically acceptable carrier or diluent. For example, it may be formulated for intracranial, parenteral, intravenous, intramuscular, subcutaneous, transdermal or oral administration. A physician will be able to determine the required route of administration for each particular patient. The pharmaceutical carrier or diluent may be, for example, an isotonic solution. The dose of product may be determined according to various parameters, especially according to the substance used; the age, weight and condition of the patient to be treated; the route of administration; the severity of the disease, and the required regimen. A suitable dose may however be from 0.1 to 100 mg/kg body weight such as 1 to 40 mg/kg body weight. Again, a physician will be able to determine the required route of administration and dosage for any particular patient.

The applicant herein demonstrates that the transgenic non-human animal model of the invention presents an enhanced local innervation in the skin and an increased density of nociceptive neurons in the skin (see FIGS. 9 and 11). The transgenic non-human animal model may thus be used as a model of pain.

The present invention thus further relates to an in vivo method for screening a candidate compound for treating pain comprising i) administering said model with the candidate compound ii) characterizing the phenotype of said model after the administration of the candidate compound and iii) positively selecting the candidate compound that prevents, reduces, reverses or delays pain in said transgenic non-human animal model as compared to the control.

The present invention also provides a kit for screening a candidate compound for use as a drug for the treatment or prevention of Neurofibromatosis type 1, which kit comprises a transgenic non-human animal model of the invention and means for determining whether the candidate compound ameliorate the phenotype of the transgenic non-human animal model.

The present invention also provides a kit for screening a candidate compound for use as a drug for the treatment or prevention of cutaneous NFB (cNB), which kit comprises a transgenic non-human animal model of the invention and means for determining whether the candidate compound ameliorate the phenotype of the transgenic non-human animal model.

The present invention also provides a kit for screening a candidate compound for use as a drug for the treatment or prevention of plexiform NFB (pNFB), which kit comprises a transgenic non-human animal model of the invention and means for determining whether the candidate compound ameliorate the phenotype of the transgenic non-human animal model.

The present invention also provides a kit for screening a candidate compound for use as a drug for the treatment or prevention of myeloid leukaemia, which kit comprises a transgenic non-human animal model of the invention and means for determining whether the candidate compound ameliorate the phenotype of the transgenic non-human animal model.

The present invention also provides a kit for screening a candidate compound for use as a drug for the treatment or prevention of malignant peripheral nerve sheath tumours, which kit comprises a transgenic non-human animal model of the invention and means for determining whether the candidate compound ameliorate the phenotype of the transgenic non-human animal model.

The present invention also provides a kit for screening a candidate compound for use as a drug for the treatment or prevention of Lisch nodules and hamartoma of the retina, which kit comprises a transgenic non-human animal model of the invention and means for determining whether the candidate compound ameliorate the phenotype of the transgenic non-human animal model.

The present invention also provides a kit for screening a candidate compound for use as a drug for the treatment or prevention of cognitive dysfunction (e.g., of learning disability, lethargy and loss of attention), which kit comprises a transgenic non-human animal model of the invention and means for determining whether the candidate compound ameliorate the phenotype of the transgenic non-human animal model.

The present invention also provides a kit for screening a candidate compound for use as a drug for the treatment or prevention of pseudoarthrosis (in particular of long bones), which kit comprises a transgenic non-human animal model of the invention and means for determining whether the candidate compound ameliorate the phenotype of the transgenic non-human animal model.

The present invention also provides a kit for screening a candidate compound for use as a drug for the treatment or prevention of splenomegaly, which kit comprises a transgenic non-human animal model of the invention and means for determining whether the candidate compound ameliorate the phenotype of the transgenic non-human animal model.

The present invention also provides a kit for screening a candidate compound for use as a drug for the treatment or prevention of spontaneous malignant transformation of neurofibromas, which kit comprises a transgenic non-human animal model of the invention and means for determining whether the candidate compound ameliorate the phenotype of the transgenic non-human animal model.

The present invention also provides a kit for screening a candidate compound for use as a drug for the treatment or prevention of pain, which kit comprises a transgenic non-human animal model of the invention and means for determining whether the candidate compound ameliorate the phenotype of the transgenic non-human animal model.

In one embodiment, the transgenic non-human animal model of the invention is for studying Neurofibromatosis type 1. In one embodiment, the transgenic non-human animal model of the invention is for studying the development of Neurofibromatosis type 1. In one embodiment, the transgenic non-human animal model of the invention is for studying NFB development, in particular cNFB or pNFB development, in Neurofibromatosis type 1. More specifically, the model of the invention may be used for studying tumour size, tumour growth, tumour number and tumour recurrence in Neurofibromatosis type 1.

Accordingly, the present invention further relates to the use of the transgenic non-human animal model as described herein for in vivo labelling of cutaneous and plexiform neurofibroma (NFB) cellular components. In one embodiment, cellular components of NFBs may be detected by immunochemistry after the sacrifice of the transgenic non-human model of the invention.

In one embodiment, NFB is cutaneous NFB and said immunochemistry is performed on skin lesions with a panel of markers directed to axonal, glial, fibroblastic and immune cells, including but not limited to Tuj1, S100, Sox10, Vimentin, Fibronectin, c-kit and Iba1.

In one embodiment, NFB is plexiform NFB and is detected in the hypodermis and on the spinal nerve roots. In one preferred embodiment, cellular components of plexiform NFBs are detected at the cervical level. In another preferred embodiment, cellular components of plexiform NFBs are detected at the thoracic level.

In one embodiment, cellular components of plexiform NFBs are characterised by immunohistochemical analysis with a panel of markers directed to axonal, glial, and immune cells, including but not limited to S100, Sox10, Vimentin, Fibronectin, c-kit and Iba1.

The present invention further relates to the use of the transgenic non-human animal model as described herein for in vivo studying cell differentiation, proliferation and/or migration in Neurofibromatosis type 1, in particular differentiation, proliferation and/or migration of Prss56-expressing cells and derivatives thereof, such as, for example, differentiation, proliferation and/or migration of BC cells or derivatives thereof in the peripheral nervous system.

In one embodiment, cell proliferation may be detected by histopathological analysis of tissues obtained from the transgenic non-human model of the invention.

In one embodiment, the migration of Prss56-expressing cells and derivatives thereof may be observed by in vivo fate mapping analyses, performed on the transgenic non-human model of the invention.

In one embodiment, the skins of control (i.e., wild-type non-transgenic animal) and of transgenic non-human model of the invention are analysed at different developmental time points.

The present invention further relates to a Prss56-expressing cell or to a derivative thereof, in particular of a BC cell or a derivative thereof, wherein the Nf1 gene is specifically inactivated.

In one embodiment, the Prss56-expressing cell or derivative thereof of the invention expresses the Cre recombinase under the control of a Prss56 promoter.

In one embodiment, the Prss56-expressing cell or derivative thereof of the invention comprises a genetic construct Prss56$^{Cre}$ in which the Cre recombinase coding sequence is inserted into the locus of Prss56, thereby resulting in the expression of the Cre recombinase under the control of the Prss56 promoter.

In one embodiment, the Nf1 gene in the Prss56-expressing cells or derivative thereof of the invention was floxed, and the expression of Prss56 has resulted in the deletion of a part of or the totality of the Nf1 gene, as described hereinabove.

In one embodiment, the Prss56-expressing cell or derivative thereof of the invention further comprises at least one reporter gene as described hereinabove, such as, for example, a reporter gene expressed under the control of a Prss56 promoter or a Cre-activable reporter gene.

In one embodiment, the Prss56-expressing cell or derivative thereof of the invention is obtained from the transgenic non-human animal model of the invention. In one embodiment, the Prss56-expressing cell or derivative thereof is harvested from the transgenic non-human animal model of the invention by dissection, and enzymatic or mechanic treatment of the recovered tissue sample (e.g., pipette disruption, trypsin digestion, collagenase digestion, etc.). In one embodiment, the Prss56-expressing cell or derivative thereof of the invention is obtained through in vitro genetic engineering of BC cells, preferably by transfection with at least one expression vector, or by CRISPR gene silencing or activation.

In one embodiment, the Prss56-expressing cell or derivative thereof expresses at least one fluorescent reporter gene and may be separated from the other cell types of the transgenic non-human animal model of the invention by a fluorescent technique, such as, for example, by flow cytometry (including fluorescence-activated cell sorting).

The present invention further relates to an in vitro method of producing cutaneous and/or plexiform NFBs, comprising culturing in vitro Prss56-expressing cells and derivatives thereof harvested from the transgenic non-human model of the invention. Indeed, the inventors herein show that the proliferation of BC cells comprising an inactivated Nf1 gene leads to NFB development. In one embodiment, the Prss56-expressing cells and derivatives thereof are cultured in a biomaterial, thereby resulting in 3D structures.

In one embodiment, Prss56-expressing cells and derivatives thereof are obtained from tissues from the transgenic non-human model of the invention, including, but not limited to, skin (e.g., skin lesions), hypodermis, nerve roots (e.g., spinal nerve roots) and dorsal root ganglia. In one embodiment, said tissue is the peripheral nervous system, and the Prss56-expressing cells and derivatives thereof are BC cells and derivatives thereof.

In one embodiment, Prss56-expressing cells and derivatives thereof are obtained by enzymatic or mechanic treatment of said tissues (e.g., pipette disruption, trypsin digestion, collagenase digestion, etc. . . . ), followed by culture under appropriate conditions, such as, for example, on a biomaterial.

The invention also relates to an in vitro method for screening a candidate compound for use as a drug for treating or preventing cutaneous and/or plexiform NFBs, comprising i) culturing in vitro Prss56-expressing cells or derivatives thereof derived from tissues obtained from the transgenic non-human model of the invention, ii) contacting said cells with the candidate compound or with a control (e.g., the vehicle), and iii) selecting the candidate compound that prevents, reduces, reverses or delays the development of NFBs, or that prevents, reduces, reverses or delays the proliferation of Prss56-expressing cells or derivatives thereof, in particular of BC cells or derivatives thereof in a significant manner as compared to the control.

The present invention further relates to an ex vivo method for studying the molecular and cellular events associated with Neurofibromatosis type I comprising comparing cells and/or tissues previously harvested from a transgenic non-human model as described hereinabove to cells and/or tissues previously harvested from a non-human animal wild-type for the Nf1 gene.

The present invention further relates to a method for identifying a compound with potential for treatment of Neurofibromatosis type 1, wherein said method comprises administering the compound to the transgenic non-human animal of the invention. In one embodiment, the method of the invention comprises comparing the phenotype of the animal administered with the compound with a control animal that did not received the compound.

Examples of phenotypes that may be assessed in the method of the invention, or of phenotype that may be characterised include, without limitation: presence and/or development of cutaneous NFB (cNFB), presence and/or development of plexiform NFB (pNFB), presence and/or development of CNS tumours, presence and/or development of myeloid leukaemia, presence and/or development of malignant peripheral nerve sheath tumours, presence and/or development of optic nerve glioma, optic nerve astrocytomas, Lisch nodules and hamartoma of the retina, presence and/or evolution of cognitive dysfunctions (e.g., of learning disability, lethargy and loss of attention), presence and/or development of pseudarthrosis (in particular of long bones), presence and/or development of scoliosis, presence and/or development of splenomegaly, spontaneous malignant transformation of neurofibromas and the like.

In one embodiment, the phenotype that is assessed in the method of the invention, or the phenotype that is characterised is selected from the presence and/or development of cutaneous NFB (cNFB), presence and/or development of plexiform NFB (pNFB), presence and/or development of CNS tumours, presence and/or development of myeloid leukaemia, presence and/or development of malignant peripheral nerve sheath tumours, Lisch nodules and hamartoma of the retina, presence and/or evolution of cognitive dysfunctions (e.g., of learning disability, lethargy and loss of attention), presence and/or development of pseudarthrosis (in particular of long bones), presence and/or development of splenomegaly, spontaneous malignant transformation of neurofibromas and the like.

The present invention further relates to a method for identifying a compound with potential for treatment of cutaneous NFB (cNFB), wherein said method comprises administering the compound to the transgenic non-human animal of the invention. In one embodiment, the method of the invention comprises comparing the phenotype of the animal administered with the compound with a control animal that did not received the compound.

The present invention further relates to a method for identifying a compound with potential for treatment of plexiform NFB (pNFB), wherein said method comprises administering the compound to the transgenic non-human animal of the invention. In one embodiment, the method of the invention comprises comparing the phenotype of the animal administered with the compound with a control animal that did not received the compound.

The present invention further relates to a method for identifying a compound with potential for treatment of myeloid leukaemia, wherein said method comprises administering the compound to the transgenic non-human animal of the invention. In one embodiment, the method of the invention comprises comparing the phenotype of the animal administered with the compound with a control animal that did not received the compound.

The present invention further relates to a method for identifying a compound with potential for treatment of malignant peripheral nerve sheath tumours, wherein said method comprises administering the compound to the transgenic non-human animal of the invention. In one embodiment, the method of the invention comprises comparing the phenotype of the animal administered with the compound with a control animal that did not received the compound.

The present invention further relates to a method for identifying a compound with potential for treatment of Lisch nodules and/or hamartoma of the retina, wherein said method comprises administering the compound to the transgenic non-human animal of the invention. In one embodiment, the method of the invention comprises comparing the phenotype of the animal administered with the compound with a control animal that did not received the compound.

The present invention further relates to a method for identifying a compound with potential for treatment of cognitive dysfunctions (e.g., of learning disability, lethargy and loss of attention), wherein said method comprises administering the compound to the transgenic non-human animal of the invention. In one embodiment, the method of the invention comprises comparing the phenotype of the animal administered with the compound with a control animal that did not received the compound.

The present invention further relates to a method for identifying a compound with potential for treatment of pseudarthrosis (in particular of long bones), wherein said method comprises administering the compound to the transgenic non-human animal of the invention. In one embodiment, the method of the invention comprises comparing the phenotype of the animal administered with the compound with a control animal that did not received the compound.

The present invention further relates to a method for identifying a compound with potential for treatment of splenomegaly, wherein said method comprises administering the compound to the transgenic non-human animal of the invention. In one embodiment, the method of the invention comprises comparing the phenotype of the animal administered with the compound with a control animal that did not received the compound.

The present invention further relates to a method for identifying a compound with potential for treatment of spontaneous malignant transformation of neurofibromas, wherein said method comprises administering the compound to the transgenic non-human animal of the invention. In one embodiment, the method of the invention comprises comparing the phenotype of the animal administered with the compound with a control animal that did not received the compound.

The present invention further relates to a method for identifying a compound with potential for treatment of pain, wherein said method comprises administering the compound to the transgenic non-human animal of the invention. In one embodiment, the method of the invention comprises comparing the phenotype of the animal administered with the compound with a control animal that did not received the compound.

The present invention further relates to a method for identifying a compound with potential for treatment of Neurofibromatosis type 1, wherein said method comprises contacting the compound with (i) Prss56-expressing cells or derivatives thereof harvested from transgenic non-human animal of the invention, or (ii) Prss56-expressing cells or derivatives thereof wherein the Nf1 gene is specifically inactivated. In one embodiment, the method of the invention comprises comparing the growth and/or proliferation of cells contacted with the compound with control cells that were not contacted with the compound.

The present invention further relates to a method for identifying a compound with potential for treatment of Neurofibromatosis type 1, wherein said method comprises contacting the compound with NFB obtained from the culture of Prss56-expressing cells and derivatives thereof wherein the Nf1 gene is inactivated. In one embodiment, said Prss56-expressing cells were harvested from transgenic non-human animal of the invention. In one embodiment, the method of the invention comprises comparing the growth and/or invasion of NFB contacted with the compound with control NFB that were not contacted with the compound.

EXAMPLES

The present invention is further illustrated by the following examples.

Materials and Methods

Animals

Mice were housed in a temperature- and humidity-controlled vivarium on a 12-h dark-light cycle with free access to food and water. The following mouse lines were used and genotyped as described in original publications: Nf1$^{fl/fl}$ and Nf1$^{fl/-}$ (Zhu et al., Science. 2002 May 3; 296(5569): 920-922), Prss56$^{Cre}$ (Gresset et al., Stem Cell Reports. 2015 Aug. 11; 5(2):278-90), R26$^{tdTom}$ (Madisen et al., Nat Neurosci. 2010 January; 13(1):133-40).

We bred Prss56$^{Cre}$:R26$^{tdTom}$ mice onto the Nf1$^{fl/fl}$ background to obtain the F1 generation (Prss56$^{Cre/+}$:R26$^{tdTom/+}$: NF1$^{fl/+}$); we bred F1 mice with Nf1$^{fl/fl}$ or Nf1$^{+/-}$ mice to obtain Prss56$^{Cre/+}$:R26$^{tdTom/+}$:NF1$^{fl/fl}$ and Prss56$^{Cre/+}$: R26$^{tdTom/+}$:NF1$^{fl/-}$ mutants, respectively. Littermates with a genotype Prss56$^{Cre/+}$:R26$^{tdTom/+}$:NF1$^{fl/+}$ were used as controls.

For analysis of embryos, the morning of appearance of a vaginal plug was designated as embryonic day 0.5 (E0.5).

All animal manipulations were approved by a French Ethical Committee and were performed according to French and European Union regulations.

Histology & Immunohistochemistry

Mice were perfused with 4% paraformaldehyde (PFA, Electron Microscopy Sciences) in 0.1 M phosphate buffer. Dorsal skin, subcutaneous nerves and nerve roots were immersed in the same fixative overnight at 4° C., and cryopreserved in 30% sucrose prior to embedding in OCT (Sakura). 12 μm-(nerves) and 20 μm-(skin) thick sections were cut on Leica cryostat. Immunofluorescence was performed as previously described (Gresset et al., 2015). The cell nuclei were counterstained with Hoechst (Life Technologies). For whole-mount immunolabeling, dorsal skin of E13.5 and E15.5 embryos and DRGs from newborn pups were dissected and fixed in 4% PFA. samples were blocked overnight in 4% bovine serum albumin (BSA) (Sigma Aldrich) in PBS containing 0.3% Triton-X-100 (PBST) (Sigma Aldrich), then incubated for 48 h with the primary antibody/BSA/PBST solution at 4° C. After rinsing secondary antibodies were applied overnight at room temperature. Samples were then washed and flat-mounted in Fluromount-G (SouthernBiotech). Whole-mount immunostaining and clarification of adult skin was performed using the iDISCO+ method, as described (https://idisco.info/idisco-protocol). Z-stacks were acquired using a Leica TCS SP5 laser-scanning confocal microscope and assembled in ImageJ and Photoshop CS6 (Adobe).

The following primary antibodies were used: rat anti-tdTOM (1:500, Kerafast #EST203), rabbit anti-dsRED (1:500, Clontech #632496), goat anti-mCHERRY (1:500, Sicgen #AB0040-200) for detection of TOM, rabbit anti-S100 (1:400, Dako #Z0311), mouse biotinylated anti-βIII-tubulin (clone TUJ-1) (1:500, R&D #BAM1195), goat anti-SOX10 (1:100, Santa Cruz #sc-17342), goat anti-SOX2 (1:100, R&D #AF2018), goat anti-cKIT (1:100, R&D #AF1356), rabbit anti-IBA1 (1:400, Wako #019-19741), goat anti-PDGFRα (1:100, R&D #AF1062), goat anti-MITF (1:300, R&D #AF5769), goat anti-TRP2 (1:100 Santa Cruz #sc-10451), rabbit anti-CGRP (1:1000, Immunostar #24112), rabbit anti-PHH3 (1:400, Abcam #ab5176), rat anti-PECAM (1:100, BD Biosciences #553370), rabbit anti- (1:200, Merck #AB5320), chicken anti-K15 (1:100, Biolegned #833901), rat ani-MBP (1:80, Merck #MAB386). Alexa 549-, Alexa 488- and Alexa 647-conjugated secondary antibodies were from Jackson Immuno Research.

Electron Microscopy

For ultrastructure analysis, mice were perfused with 2% paraformaldehyde/0.5% glutaraldehyde or with 4% paraformaldehyde/1.6% glutaraldehyde (Polysciences) in 0.1 M phosphate buffer. Dorsal skin, nerve roots and subcutaneous nerves were dissected and post-fixed in the same solution overnight at 4° C. followed by embedding.

For standard electron microscopy, samples were embedded in Epon (EMbed 812, Electron Microscopy Sciences, Ref. 14900) as previously described (Gresset et al., 2015). Semi-thin sections (1 μm) were labelled with toluidine blue and ultra-thin sections were analyzed using a Tecnai electron microscope or a Jeol microscope.

For immuno-electron microscopy, fixed samples were embedded in LR White Hard Grade (Electron Microscopy Sciences, Ref. 14383) as described. tdTom-expressing cells were detected using rabbit anti-RFP antibody (1:50, Rockland, Ref. 600-401-379). TOM-expressing cells were detected using rabbit anti-RFP antibody (1:20, Rockland #600-401-379).

Skin Incisions 3-month-old control and Nf1-KO mice were anesthetized with Isoflurane. Dorsal skin at the lateral thoracic level was shaved, disinfected with 70% ethanol and 5 mm long incisions were performed with micro-scissors. Incisions were sutured and mice were placed back in the cage. After 7 months, the animals were sacrificed and perfused with 4% paraformaldehyde (PFA). The back skin was dissected and processed for immunohistochemical analysis.

Fluorescence-Activated Cell Sorting

To purify TOM-expressing cells, newborn back skin of $Prss56^{Cre}$, $R26^{tdTom}$, $Nf1^{fl/fl}$ mice was dissected free of other tissues and digested with collagenase/dispase type I (Sigma/Roche) for 2 h at 37° C., followed by mechanical dissociation and filtration. The resulting cell suspension ($3\times10^6$ cells/ml) was purified on a FacsVantage (Becton Dickinson) equipped with an argon laser tuned to 561 nm. Dead cells and doublets were excluded by gating on a forward-scatter and side-scatter area versus width. Log RFP fluorescence was acquired through a 530/30 nm band pass. Internal TOM-negative cells served as negative controls for FACS gating. Equal number of TOM-positive and TOM-negative cells were sorted directly into RNAlater (Ambion) and stored at −80° C. until further processing.

RNA Extraction and Semi-Quantitative RT-PCR

Total RNA was isolated from FACS-sorted TOM-positive and TOM-negative cell fractions using the RNAqueous-Micro kit (Thermo Fisher Scientific) according to the manufacturer's instructions. Adult Nf1-KO mutant skin and E12.5 neural tube (with BCs) were mechanically dissociated using a MM300 TissueLyser (Qiagen) and RNA was extracted using the RNeasy Fibrous Tissue kit (Qiagen) according to the manufacturer's instructions. Total RNA (100 ng) was reverse transcribed using pSuperscript III Rnase H reverse transcriptase (Invitrogen) and a mix of oligo-dT and random primers (Invitrogen), according to the manufacturer's instructions. PCR was performed as follows: 2 min at 94° C.; 30 cycles of 2 min at 94° C., 1 min at the primer-specific annealing temperature, 1 min at 72° C.; and 10 min at 72° C. The sequences of forward (F) and reverse (R) primers, primer annealing temperature (° C.) and expected product size (bp) are as follows: β-actin (Forward primer: TGTTACCAACTGGGACGACA SEQ ID NO: 15, (Reverse primer: GGGGTGTTGAAGGTCTCAAA SEQ ID NO: 16, 60° C., 165 bp), Prss56 (Forward primer: GGTCTTCAGTGGCCTAGTGG SEQ ID NO: 3, Reverse primer: AGCCTCTGTCCTTGATCAGC SEQ ID NO: 4, 58° C., 151 bp), Nf1 (Forward primer: GCTTCCCTCAGAACAGCATC SEQ ID NO: 17, Reverse primer: GCCCCTTTCAATTCTAGGTGG SEQ ID NO: 18, 58.5° C., 128 bp). For each RNA sample, two independent PCR amplifications were performed.

Sirius Red Staining of Collagen

For collagen staining, fixed dorsal skin was embedded in paraffin and 5 μm thick sections were cut. Paraffin sections were deparaffinised and rehydrated, stained with Weigert's hematoxylin (Sigma Aldrich) for 8 minutes, and washed in water. They were subsequently stained in Picro-sirius red (Sigma Aldrich) for one hour, washed in two changes of acidified water, dehydrated, cleared in xylene and mounted in a resinous medium. Bright-field images were acquired using a Leica DM 5500B microscope.

Cell Quantification and Statistical Analysis

Quantifications of dermal cell populations were performed on whole-mount preparations (embryonic skin) and on cryostat sections (newborn, P9 and P90 skin) of Nf1-KO (n=3) mutants and control littermates (n=3). At least two skin biopsies and 4 distant sections of postnatal skin (from the same A-P level) were selected from each individual and subjected to immunolabelling with cell type-relevant antibodies. 40 μm- or 20 μm-thick z-stacks (for whole-mounts and skin sections, respectively) were acquired using a Leica TCS SP5 laser scanning confocal microscope, and the number of cells (containing nuclei) were quantified using 6 to 12 fields from each sample. The scanned surface area corresponds to 0.15 μm2 for E15.5 skin and 0.38 μm2 for other samples. For sectioned samples, upper and lower tissue limits were defined by the epidermis and the panniculus carnosus muscle, respectively. For quantification of the melanocyte lineage, only fields containing a minimum of one traced melanocyte of any kind (follicular or extrafollicular) were included in the analysis due to highly heterogeneous distribution patterns. Cell counting in 6-month-old skin was performed using electron microscopy, based on the ultrastructural characteristics of distinct cell populations. Ultrathin sections were deposited on Copper grid and 15 grid hexagons (0.026 mm2 each) were scanned for each individual (3 Nf1-KO and 3 controls). Quantification of TOM+/SOX10+ cell fractions in the adult cervical nerve roots was performed on 20 μm-thick longitudinal sections of $Prss56^{Cre}$, $R26^{tdTom}$ mice (n=3). Cell counts were normalised against the total number of SOX10+ cells. Quantification of traced sensory neurons was performed on whole-mount preparations of cervical dorsal root ganglia isolated from Nf1-KO (n=3) and control (n=3) newborn pups and immunolabelled for TOM and TUJ1. Acquired z-stacks were screened for the presence of TOM-positive neuronal perikarya, based on morphological criteria. Statistical analyses were carried out using two-tailed Student t-tests or non-parametric Mann-Whitney tests (for quantification of the melanocyte lineage and electron microscopy-based counting), and p-values considered significant are indicated by asterisks as follows: *p<0.05, p<0.01, and *p<0.001. Statistical analyses and scatter plots were generated using the GraphPad Prism 6.0 package. The data are represented as mean values±standard deviation (SD) or standard error of the mean (SEM).

Analysis of Cell Proliferation

Pregnant mice were intraperitoneally injected with EdU at the dose of 20 mg per kg of body mass at embryonic age E18.5 and newborn pups were collected 24 h later. Three Nf1-KO and two control littermates were decapitated, and their skin was dissected and fixed overnight in 4% PFA. Cryostat sections were prepared as described above. EdU detection was performed using the Click-IT Plus EdU Alexa Fluor 488 Imaging Kit (Thermo Fisher Scientific) according to the manufacturer's instructions, followed by immunolabelling for TOM and TRP2. Numbers of proliferating Schwann cells (TOM+/TRP2−/EdU+) were normalised against the total number of traced (TOM+/TRP2−) SCs. Quantifications were performed on 4 distant sections from each individual (~24 fields per sample) using 25× magnification under a TCS SP5 confocal microscope. The two-tailed Mann-Whitney test was used for statistical analysis. P values<0.05 were considered statistically significant.

Results

Prss56-expressing BC Cells Give Rise to Schwann Cells and Endoneurial Fibroblasts in Nerve Roots and Nerve Terminals in the Skin We have characterised the progeny of Prss56-expressing BC cells (by means of tdTom expression) in the spinal nerves of adult mice, focusing on nerve roots and cutaneous nerve terminals, where neurofibromas commonly develop in NF1 patients. Immunohistochemical analysis of tdTom-traced cells in nerve roots revealed the presence of both myelinating (mSC) and non-myelinating Schwann cells (non-mSC), characterised by S100β and Sox10 immunoreactivity (data not shown), two SC-specific markers.

Of note, expression level of S100β, commonly used as a marker of SC lineage, varied significantly between mSCs and non-mSCs, with the later population being much weakly labelled. A similar phenomenon has previously been described in the rodent sciatic nerve (Mata et al., J Neurocytol. 1990 June; 19(3):432-42). Thus, in order to differentiate between non-mSCs and endoneurial fibroblasts (EFBs) that lack S100β immunoreactivity (and for which unique molecular makers have not yet been identified), we used combined immunohistochemical and electron microscopy approach (FIG. 1 and data not shown). This study ultimately confined tdTom expression to a subset of mSCs and non-mSCs (characterised by continuous basal lamina) as well as EFBs (that lack basal lamina). Conversely, we have never observed tdTom-positive perineurial fibroblasts, in line with their non-neural crest origin (Joseph et al., Development. 2004 November; 131(22):5599-612).

Figure 2:
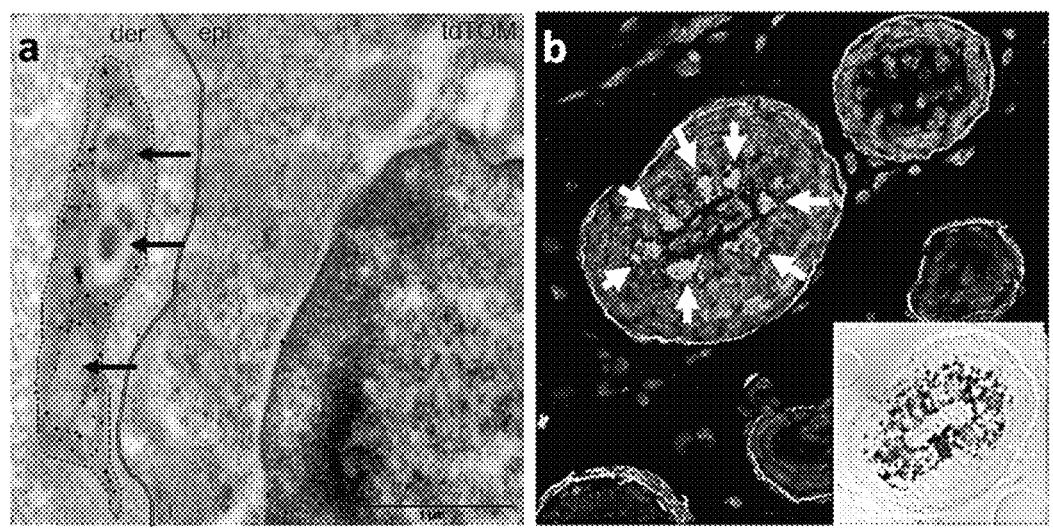
FIG. 2 is an electronic microscopy ultrathin section (a) and an immunohistochemistry cryosection (b), showing the fate mapping of BC cell derivatives in the nerves innervating skin. a. Majority of tdTom-expressing cells (black dots in the dotted line area) are localised in the dermis (der) and hypodermis (not shown), remain in close contact with nerves (black arrows), and correspond to non-myelinating, lanceolate and subepidermal Schwann cells. epi: epidermis; der: dermis. b. Cryosection showing the presence of tdTom-expressing pigmented cells (white arrows) in the hair bulb that correspond to melanocytes.

In the skin, tdTom-traced cells were found exclusively in the hypodermis (subcutis) and dermis, and showed a highly heterogeneous distribution, with groups/patches of cells aligned with some, but not all, nerves and nerve terminals. Great majority of them corresponds to SCs based on the synthesis of S100β and continuous basal lamina. Notably, the proportion of mSCs vs non-mSCs is markedly reduced in dermis (as compared to the hypodermis or nerve roots) where large, myelinated fibres are scarce. On the other hand, dermal non-mSCs are highly heterogeneous and include several morphologically and topologically distinct categories such as the "classical" nerve-associated SCs as well as two types of terminal SCs: hair follicle-associated lanceolate glia and nociceptive fibre-associated SCs that reside directly beneath the epidermis, thus further referred to as subepidermal SCs (SSCs). Finally, tdTom expression was present in a fraction of hair bulb melanocytes and EFBs populating subcutaneous and dermal nerves (Gresset et al., Stem Cell Reports. 2015 Aug. 11; 5(2):278-90 and FIG. 2).

Nf1 Loss in Prss56-Expressing BC Cells is Sufficient for Neurofibroma Development Since derivatives of Prss56-expressing BCs populate targets highly privileged for NFB formation, such as nerve roots and cutaneous nerve terminals, we sought to determine whether Nf1 loss in BCs gives rise to plexiform (paraspinal) and cutaneous NFBs. To explore this possibility, we bred $Prss56^{Cre/+}:R26^{tdTom/+}$ mice into a $Nf1^{fl/fl}$ or $Nf1^{fl/-}$ background to generate $Prss56^{Cre/+}:R26^{tdTom/+}:Nf1^{fl/fl}$ and $Prss56^{Cre/+}:R26^{tdTom/+}:Nf1^{fl/-}$ progeny, collectively referred to as Nf1-KO mice. These animals carried biallelic Nf1 inactivation in BCs and all their derivatives in a Nf1 heterozygous or wild-type environment, respectively. In addition, Cre-driven expression of a fluorescent reporter (tdTom) enabled in vivo tracing of Nf1 mutant cells throughout development. As controls, we used $Prss56^{Cre/+}:R26^{tdTom/+}:Nf1^{fl/+}$ littermates (CTRL) carrying heterozygous Nf1 inactivation in BCs on a wild-type background. All CTRLs were phenotypically undistinguishable from the $Prss56^{Cre/+}:R26^{tdTom/+}$ animals and have not developed any abnormalities. The use of the two genetic backgrounds was an important consideration since in the majority of existing Nf1 GEM models, tumorigenicity requires loss of both Nf1 alleles in the cells destined to become neoplastic, along with Nf1 heterozygocity in the tumour environment. Unexpectedly, both types of mutants developed identical symptoms, including numerous skin lesions, mainly localized at the level of the neck and middle-back, and had to be euthanized due to diffuse skin pruritus or partial forelimb paralysis. The first visible symptoms typically appeared around 8 or 12 months of age (for $Nf1^{fl/-}$ and $Nf1^{fl/fl}$ backgrounds, respectively) as areas of hair thinning and rapidly evolved into scabs/crusts, often filled with liquid. After shaving off the hair, we often observed additional lesions that could reach into hundreds in aging individuals. Macroscopic analysis of the mutant skin revealed accumulation of tdTom-expressing (Nf1 mutant) cells in all skin lesions. Gross dissection revealed the presence of multiple paraspinal and subcutaneous plexiform neurofibromas in all examined individuals (Table 1).

TABLE 1

| Genotype | Plexiform (paraspinal) neurofibroma | | Cutaneous neurofibroma | |
|---|---|---|---|---|
| | Frequency | Age (min-max) | Frequency | Age (min-max) |
| $Prss56^{Cre}:R26^{tdTom}:Nf1^{fl/fl}$ | 100% (12/12) | 15.2 months (6.2-19.3) | 82.3% (14/17) | 12.8 months (6.2-19.3) |
| $Prss56^{Cre}:R26^{tdTom}:Nf1^{fl/-}$ | 100% (6/6) | 9.1 months (5.9-12.4) | 75% (6/8) | 8.6 months (2.9-12.4) |

Characterisation of Cutaneous Neurofibromas

Figure 4:
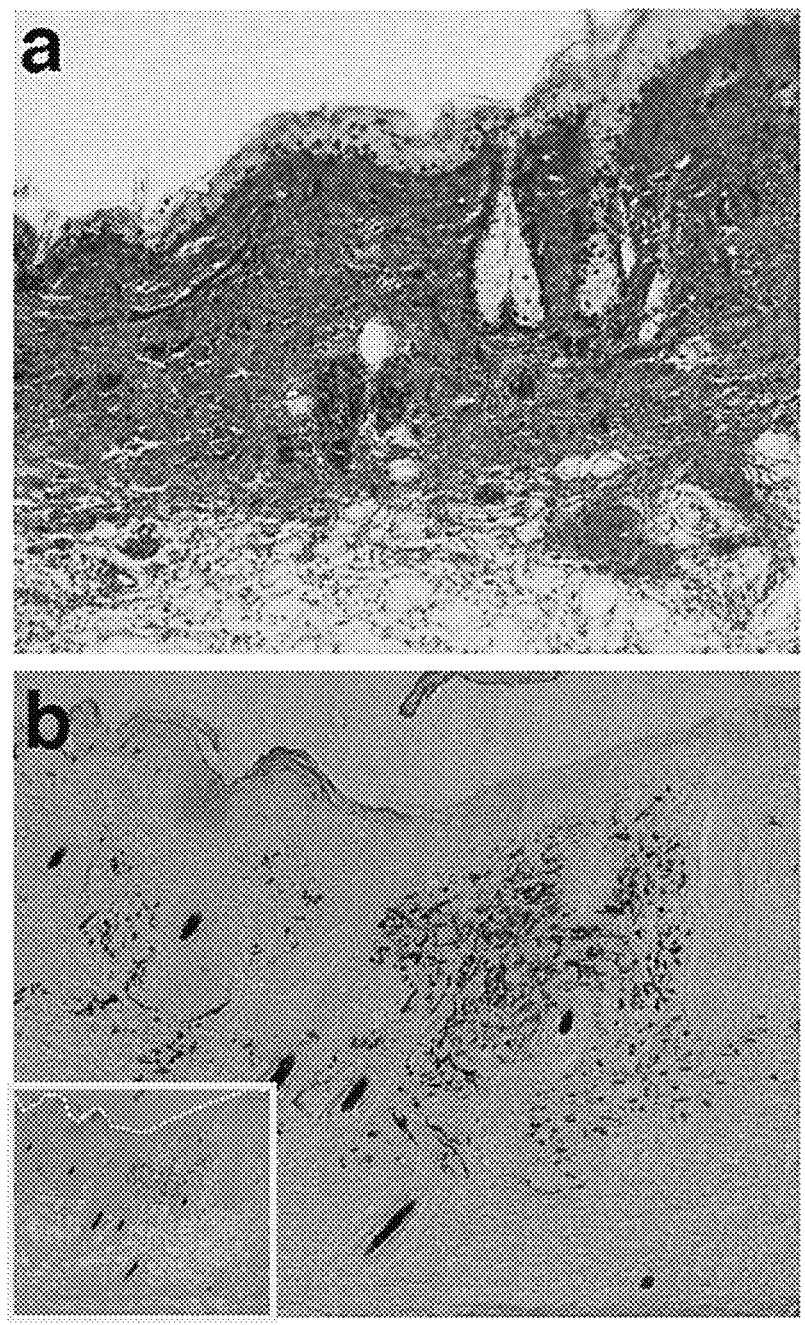
FIG. 4 is a histological analysis of the cutaneous neurofibroma in Nf1 mutant mice. Note the accumulation of collagen (a) and numerous tdTom-negative pigmented cells (b) at the level of NFB.

Cellular characterization of skin lesions was performed by immunofluorescence with markers against tdTom-expressing cells along with SCs (S100β), fibroblasts (Fibronectin), mastocytes (c-kit) and macrophages (Iba1), all present in human cNFBs (data not shown). All lesions were localized in the dermis and contained a mixture of tdTom-traced and non-traced cells. Great majority of tdTom-traced cells in the lesion correspond to S100β-expressing SCs. However, they appear highly disorganized and extend numerous slender cytoplasmic processes that were never observed in the control skin. Only a small fraction of tdTom-expressing cells lacked S100β immunoreactivity. They were usually found at the periphery of a lesion and exhibited fibroblast-like morphology. In addition, we observed increased number of non-traced, c-kit-expressing mastocytes and Iba1-expressing macrophages infiltrating the lesion (data not shown). Finally, many cNFBs contained pigmented cells (tdTom-negative) scattered through the lesion (FIG. 4), similarly to what has been observed in human cNFBs.

Figure 3:
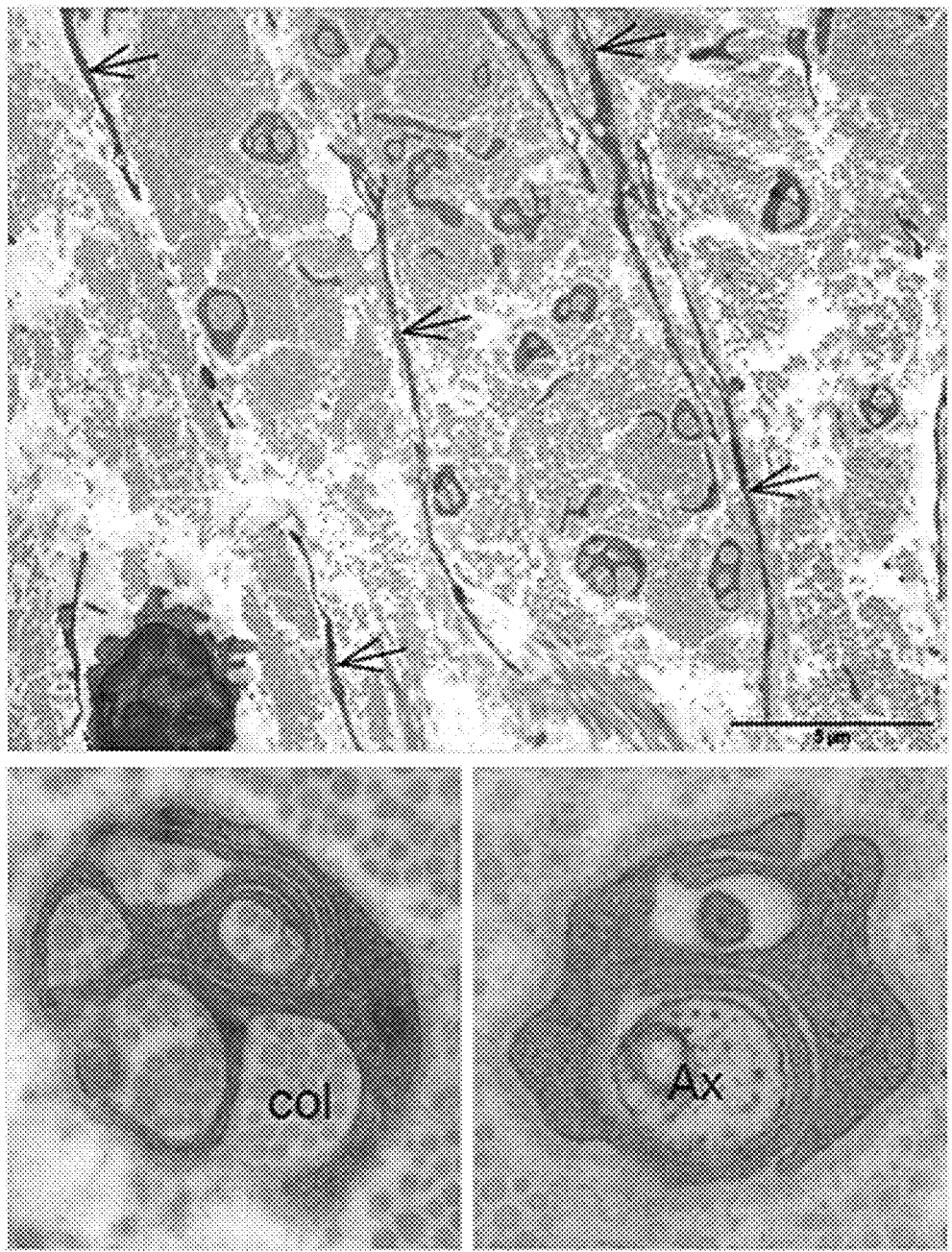
FIG. 3 shows the ultrastructure analysis of the cutaneous neurofibroma in mice carrying Nf1 loss in BC derivatives. The structure reveals the presence of numerous isolated Schwann cells with multiple cytoplasmic protrusions often enwrapping clusters of collagen fibres (top panel). Lower panel shows magnified view of a Nf1 deficient, axon-free Schwann cell (left) and a control Schwann cell (right) associated with an axon. col: collagen; Ax: axon.

More detailed ultrastructure analysis of Nf1-KO skin lesions, confirmed the presence, in the dermis, of numerous SC-like cells characterized by their continuous basal lamina. These cells were either in contact with axons or axon-free and formed a dense network of long cytoplasmic extensions that enwrapped collagen fibrils (the so-called collagen pockets) or isolated axons (FIG. 3). In addition to this surnumerary glial component, we observed accumulation of collagen fibrils (FIG. 4), fibroblasts, mastocytes and macrophages infiltrating the lesion (data not shown). Interestingly, this cellular hypertrophy was also accompanied by an increased density of innervation (data not shown). This observation was previously reported in some NF1 patients and proposed as the origin of skin hypersensitivity. Higher density of innervation in the mutant skin could be linked either to increased neurogenesis of Nf1 deficient BC-derived neuronal progenitors (in addition to SCs, BCs give rise to the subpopulation of sensory neurons) and/or to abnormal ramifications of axon terminals in the mutant dermis. Since the sensory neurogenesis is completed before birth, we have compared the number of tdTom-expressing neurons in CTRL versus Nf1-KO newborn DRGs (n=6) isolated from the same A-P level (data not shown). This analysis revealed no differences suggesting increased ramification of existing sensory axons in the Nf1-KO skin.

Of note, comparison of cNFB that are associated with pruritus (typically at the neck level) versus pruritus-free lesions (found more posteriorly and in animals that survived 1.5 years) revealed identical cellular composition, including infusion by mastocytes and macrophages. Thus, the strong inflammatory response that accompany cNFBs is not likely to be induced by pruritus itself, although it might be potentiated by pruritus. Second, pruritus is clearly a consequence, but not a cause of cNFB.

Characterization of Plexiform NFBs

Figure 5:
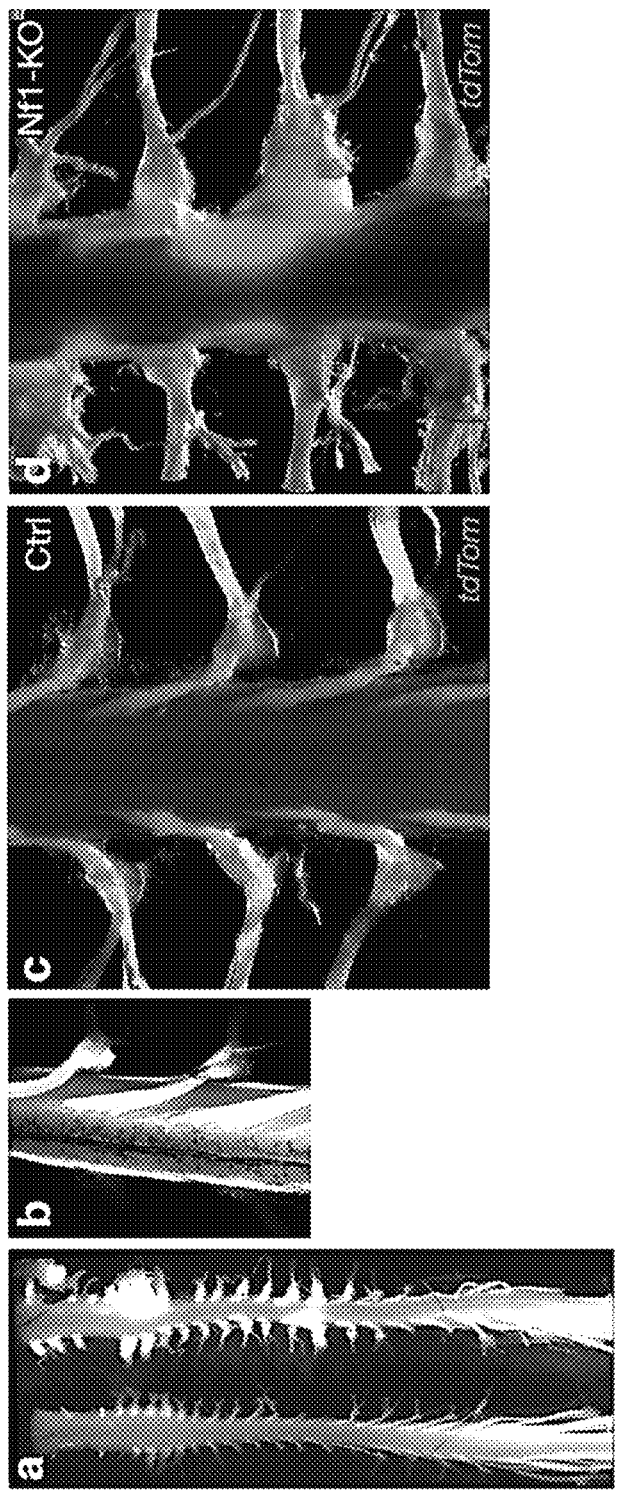
FIG. 5 is a set of 4 views of control (a, left; c) and Nf1 mutant (a, right; b; d) adult spinal cord of mice carrying Nf1 loss in BC derivatives. a. Global view of the control (left) and Nf1 mutant (right) adult spinal cord. Numerous paraspinal tumours are detectable in the mutant spinal nerve roots at the cervical and thoracic levels. b. In the Nf1 mutant, enhanced pigmentation is present around the meninges and DRGs. c, d. Higher magnification of the control (c) and Nf1 mutant (d) spinal cord at thoracic level. Nf1 mutant present accumulation of tdTom-expressing cells in the nerve roots and DRG causing nerve hyperplasia and neurofibroma compressing spinal cord.
Figure 6:
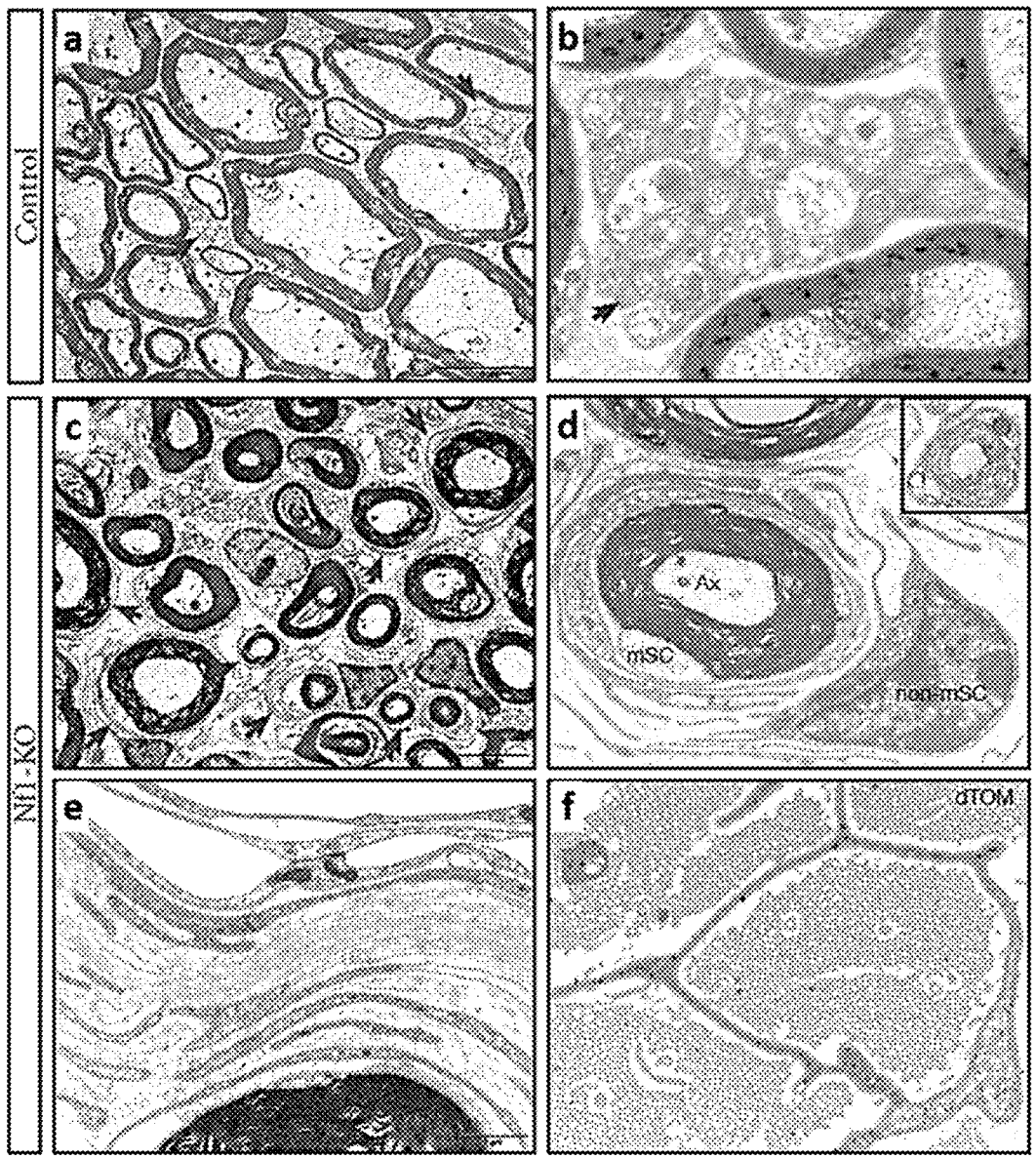
FIG. 6 is an ultrastructure analysis of control (a-b) and Nf1 mutant nerve roots (c-f). In Nf1 mutant nerve roots, non-myelinating Schwann cells form numerous cytoplasmic protrusions with some of them forming multi-lamellar structure around myelinated axons (d and e) and collagen fibres (f). tdTom-expressing cells correspond to myelinating and non-myelinating Schwann cells. Ax: axon; mSC: myelinated Schwann cells; non-mSC: non-myelinated Schwann cells.

In addition to cNFBs, NF1 KO mice develop two types of pNFBs that are localised in the hypodermis (subcutaneous pNFBs; often localised just beneath the cNFBs) (data not shown) and on the spinal nerve roots (paraspinal pNFBs) (FIG. 5). Plexiform tumours were observed on both NF1$^{fl/fl}$ and NF1$^{fl/-}$ background. Interestingly, in all mutant animals that were sacrificed beyond 6 months of age (due to severe pruritus) both types of pNFBs were detected at the cervical level. Notably, older individuals (that survived beyond 1 year) developed additional NFBs at the thoracic level indicating rostro caudal and temporal gradient in development of paraspinal pNFBs. Both, subcutaneous and paraspinal tumours contain numerous tdTom-expressing cells. Ultrastructure analysis revealed abnormal accumulation of non-mSC-like cells and endoneurial fibroblasts lying free in collagen-rich stroma. As in the cNFBs, the morphology of SCs appears profoundly affected with the dense network of cytoplasmic protrusions surrounding isolated axons, mSCs, and collagen fibres (FIG. 6). Immunohistochemical analysis with the panel of markers previously used to characterize cNFBs confirmed that Nf1 mutant SCs constitute the major cellular component of the tumour and also revealed the presence of numerous tdTom-expressing endoneurial fibroblasts and non-traced mastocytes and macrophages (data not shown). Interestingly, we have noticed that the Nf1 mutant non-mSC express S100β at much lower level than controls. However, they were positive for SC marker Sox10 and immature peripheral glia marker Sox2 suggesting their immature character (data not shown). Finally, despite markedly increased diameter of subcutaneous nerves and nerve roots at the tumour level, the perineurium remains intact suggesting that pNFBs in our model are encapsulated (in contrast to non-encapsulated NFBs in which perineurial layer is destroyed). All these observations are compatible with development of typical pNFBs.

Overall, our studies suggest that Nf1 loss in Prss56-expressing BCs and their derivatives promotes the development of cutaneous and plexiform NFBs. Furthermore, since the NFBs occur in both genetic backgrounds, heterozygocity in tumour environment does not appear necessary in our system. Finally, in addition to NFBs, all mutant mice develop marked splenomegaly (one of the symptoms of myeloid leukaemia), hamartomas of the retina and present long bone defects (data not shown), all symptoms described in some NF1 patients. In conclusion, to our knowledge, this genetic tool constitutes the first murine model that faithfully recapitulates the human NF1 disease, in particular the development of cNFBs, which have never been reported in previous animal models. As inactivation of Nf1 in the PNS is restricted to BC cells and their derivatives, this clearly identifies this population as the cellular origin of NFBs.

Figure 7:
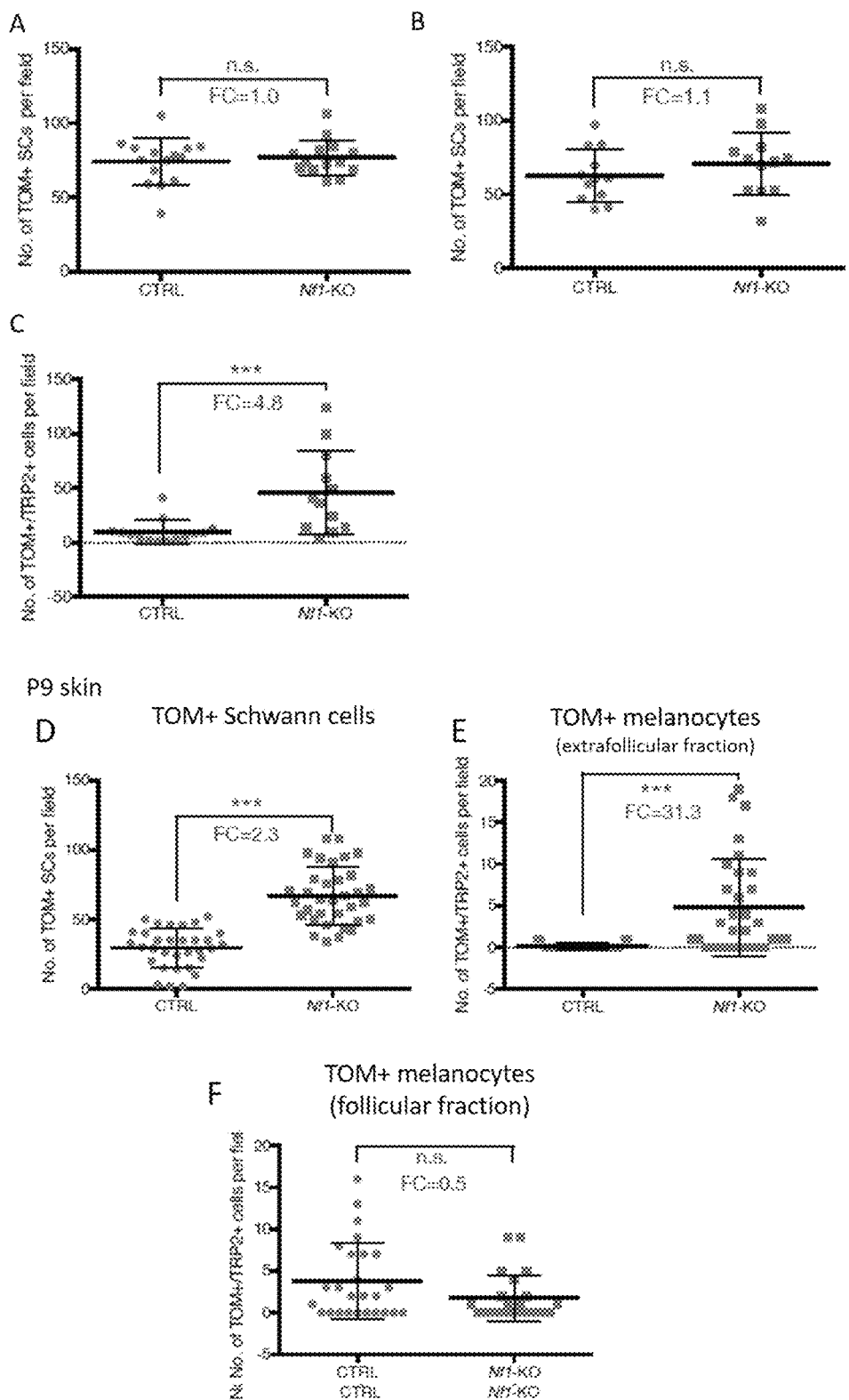
FIG. 7 represents the impact of Nf1 inactivation on the proliferation of embryonic and early postnatal BC cell-derived melanocyte and glial lineages. (A) Quantification of the number of TOMpositive/TRP2-negative cells (SC precursors) along the axons in preparations of E13.5 control (CTRL) and Nf1-KO skin immunolabelled for TOM and TUJ1. (B) Quantification of the number of TOM-positive/TRP2-negative cells (immature SCs) along the axons in preparations of E15.5 control (CTRL) and Nf1-KO skin immunolabelled for TOM and TUJ1. (C) Quantification of the number of TOM-positive/TRP2-positive cells not associated with axons (melanoblasts) in preparations of E15.5 control (CTRL) and Nf1-KO skin immunolabelled for TOM and TUJ1. (D-F) Quantification of TOM-positive SCs (D), and of extrafollicular (E) and follicular (F) melanocytes in P9 control (CTRL) and Nf1-KO mutant skin. Traced melanocytes were identified based on TOM and TRP2 expression and lack of axonal contact, while TOM-positive cells were considered SCs based on lack of TRP2 expression and association with axons. Quantification data are represented as mean values±SD.

Development of Cutaneous Neurofibromas (cNFs) Involves Progressive Alterations of the Dermis Although NF1 patients develop cNFs during adulthood after a long asymptomatic period, it is unclear whether these tumours appear suddenly in the adult skin or whether they slowly evolve from micro-tumoural loci already present at younger ages. To investigate this issue, the skin of Nf1-KO mice was compared to control littermates from embryonic day E13.5, when the first traced BC derivatives settle in the skin, until 6 months after birth, when most mutants do not show obvious cutaneous manifestations. For this study, only Prss56$^{Cre}$, R26$^{tdTom}$, Nf1$^{fl/-}$ mutants which, similar to NF1 patients, harbour heterozygous germline Nf1 mutation along with homozygous Nf1 knockout in the SC lineage, were used. The inactivation of Nf1 in BC cells around E11 did not affect the migration of BC-derived progenitors along the nerves to the skin nor the number of traced SC precursors or immature SCs in the embryonic skin (FIG. 7). This suggests that the early specification and migration of the SC lineage is not affected in the absence of Nf1. At birth, however, the number of traced SCs in Nf1-KO was nearly double that in control skin (FIG. 8A), although all mutant SCs remained in contact with axons and did not show any morphological abnormalities. Intraperitoneal 5-ethynyl-2'-deoxyuridine (EdU) injection into pregnant females at E18.5, followed by analysis of newborn skin, revealed a small but significant (p=0.036) increase in the proportion of proliferating SCs (EdU+/TOM+) in Nf1-KO (22.6±1.37%) compared to control animals (18.19±1.89%, mean±SEM). SC proliferation is later maintained in cNFs, as immunolabelling of cNFs from 10-month-old Nf1-KO mutants against the mitotic marker phospho-histone-H3 (PHH3) indicates that a small proportion of traced cells undergo mitosis (data no shown). Overall, these data suggest that inactivation of Nf1 provides a small proliferative advantage to mutant SCs.

Figure 8:
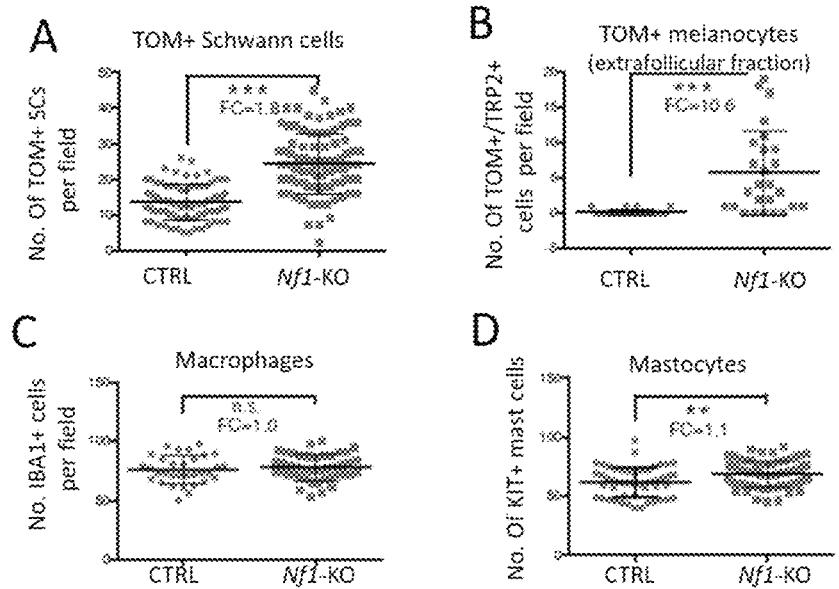
FIG. 8 represents Nf1 loss-of-function in BC cells promotes proliferation of dermal Schwann cell and melanocyte lineages. (A-D) Quantification of traced SCs (A), melanocytes (B), non-traced IBA1+ macrophages (C) and KIT+ mastocytes (D) in control vs Nf1-KO P0 skin. (E, F) Quantification of traced SCs (E) and non-traced KIT+ mastocytes (F) in the control and Nf1-KO dermis. Data are represented as mean values±SD. Each data point corresponds to a number of cells per field of view. Fold change (FC) differences are given for each comparison.
Figure 8:
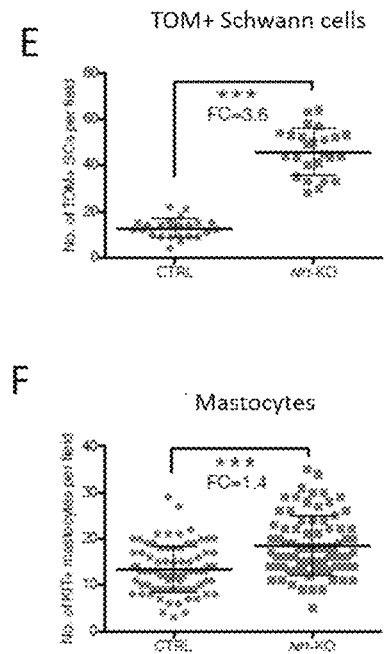

As BC-derivatives include a subset of skin melanocytes, the number of cells co-expressing TOM and the melanocyte lineage marker TRP2 between Nf1-KO were compared with control, newborn animals. While no difference is observed in the number of traced melanoblasts within the hair follicles, the extrafollicular (dermal) fraction was substantially increased in Nf1-KO skin (FIG. 8B and data not shown). Interestingly, there is already enhanced melanocytogenesis in embryonic skin at E15.5 (FIG. 7C). At P9, when melanoblasts migration into developing hair follicles is complete in control skin, numerous double-positive (TOM+/

TRP2+) cells were still observed in the mutant dermis. Conversely, there was no difference in the numbers of traced follicular melanocytes (FIG. 7E-F), suggesting a selective expansion of the extrafollicular melanocyte fraction.

Next, the elevated SC content in mutant newborn skin was investigated to see if it is accompanied by modifications of the other cell types. Although Nf1-KO skin had a slight (1.1-fold), elevation in the number of KIT+ mastocytes compared to controls (FIG. 8D), the densities of PDGFRα+ fibroblasts (data not shown) and of IBA1+ macrophages (FIG. 8C) were comparable between the two groups.

Analysis of the postnatal back skin between P0 and 3 months of age revealed a further progressive increase in the numbers of TOM+ SCs in Nf1-KO mutants compared to controls (FIG. 8E and FIG. 7D). Although at three months, most traced SCs were still well aligned with axons, many appeared hypertrophic and extended numerous cytoplasmic protrusions that detached from axons (data not shown). In some cases, we observed an entire SC soma "escaping" from the nerve bundle (data not shown). These abnormal morphologies preferentially occurred in the upper dermis (FIG. 9A-D). As in the newborn skin, the number of mastocytes was slightly (1.4-fold) higher in Nf1-KO dermis than in controls (FIG. 8F), whereas the density of macrophages was unaffected (data not shown). In contrast, a dramatic increase in the density of dermal fibroblasts was observed, as revealed by labelling for PDGFRα and increased density of nuclear staining (data not shown).

It is surprising that despite their increased number, mutant SCs mostly remain in contact with axons for up to 3 months. This observation raises the possibility of an increase in the density of cutaneous innervation to cope with increased SC numbers. To examine innervation density, whole-mount immunostaining of the 3-month-old Nf1-KO and control skin was performed with antibodies against TOM and the pan-axonal marker β-III-tubulin (TUJ1). The density of innervation appeared higher in the regions of Nf1-KO skin corresponding to patches of traced SCs as compared to controls or regions of mutant skin poor in traced cells (FIG. 9E-G). This suggests that enhanced local innervation in the mutant skin is linked to SC hyperplasia. To investigate if enhanced innervation might result from increased sensory DRG neurogenesis, the numbers of traced sensory neurons in Nf1-KO mutant was compared to control newborn DRGs from the same A-P level (FIG. 9H). There was no significant difference in the number of traced sensory neurons, suggesting that enhanced innervation is rather due to branching of nerve terminals in the mutant dermis.

Next, the skin of 6-month-old Nf1-KO mice, which still did not show any visually detectable abnormalities, was analysed. However, numerous microscopic lumps were detected upon tactile examination. Histological analysis of the skin revealed SC hyperplasia along with the presence (over the entire back skin) of multiple small (up to 1 mm) aggregates of disorganised nmSCs, positive for TOM and S100 (FIG. 10A-C), which were intermixed with numerous nontraced fibroblasts, mastocytes, macrophages and polymorphonuclear neutrophils, all present in typical cNFs. Quantification of distinct cell populations was performed by electron microscopy (FIG. 10H). Interestingly, the presence of inflammation-related cells, such as neutrophils, mastocytes and macrophages in these micro-lesions suggests these cell types are involved in the development and/or progression of tumours rather than being a simple consequence of pruritus-related inflammation. Ultrastructural characteristics of nmSCs in the micro-lesions were also typical of classical cNFs and included abnormal extension of cytoplasmic processes that enclosed isolated axons and/or groups of collagen fibrils, or were devoid of axonal contact (FIG. 10F, G). Whole-mount immunostaining of the mutant dermis confirmed accumulation of traced SCs with profound morphological aberrations (FIG. 10D-E'). SC hypertrophy in the upper dermis was far more severe than in 3-month-old mutants, and some cells seemed to lose contact with axons. In the lower dermis, most mutant SCs had detached from axons and extended multiple filipodia-like structures. Together these data indicate that the micro-lesions, apart from their size, share essential characteristics with bona fide cNFs and consequently, referred hereinafter as to micro-cNFs.

Ultrastructural examination of dermal innervation also revealed that intact Remak bundles, containing small groups of tightly packed axons, were extremely rare in the mutant dermis. Instead, numerous isolated axons that were separated by large quantities of collagen and individually ensheathed by small fragments of SC cytoplasm were commonly observed (FIG. 10G). This suggests decompaction of nerve bundles. Moreover, a 2-fold difference in axon numbers between Nf1-KO and control dermis were observed (FIG. 10H). Immunolabelling with CGRP, a marker of peptidergic nociceptive neurons further supported an increased density of dermal innervation in micro-cNFs compared to control dermis (data not shown). Overall, these data point toward a marked decompaction of nerve bundles combined with increased branching of axon terminals in the mutant dermis.

If micro-cNFs constitute a precursor stage of full-blown tumours, it would be expected that the number of tumours arising in older individuals should be much larger than what was actually observed (typically up to a few well-demarcated lesions per mutant at the cervical or cervico-thoracic level). As mutant mice had to be sacrificed as soon as pruritic lesions appeared, it is likely that most of the developing tumours did not have enough time to reach a macroscopically detectable stage. Indeed, this idea is supported by the observation of a unique Nf1-KO individual that survived until 20 months of age without developing pruritus. In this case, dozens of raised skin bumps containing dense clusters of traced cell were observed all over the back skin (data not shown). Analysis of their cellular composition with the set of markers described above confirmed their cNF identity (data not shown). This strongly supports the hypothesis that many of the micro-cNFs observed in the 6-month-old skin could evolve into full-blown diffuse cNFs in older animals.

Skin Injury Accelerates the Development of cNFs

In NF1 patients, surgical and laser ablation of cutaneous tumours are routinely used for tumour resection. However, several case reports suggest that skin injury (trauma) might promote development of additional cNFs. To test whether an injury favors the appearance of tumours, small skin incisions were made at the thoracic level on 3-month-old Nf1-KO mutants (n=6) and control individuals (n=4) (FIG. 11A). These animals were sacrificed at 10 months of age and their skin was analysed and compared with that of uninjured age-matched Nf1-KO mutants (n=6). All injured Nf1-KO mutants developed large, mostly nonpruritic lesions at the site of injury, containing large accumulations of traced cells (FIG. 11B, C).

Furthermore, all injured mutants also developed numerous, smaller (≤5 mm), well-demarcated lesions all over the back skin (FIG. 11E). Both types of lesions, at the injury site or distant from it, corresponded to very dense accumulations of TOM+ cells (FIG. 11C, F, I, J). Thoracic and lumbar lesions were histologically identical (except for their size)

and corresponded to typical diffuse cNFs (FIG. 11I, J and data not shown). No abnormalities in the distribution or densities of traced cells were ever observed in injured control animals (FIG. 11D and data not shown). Moreover, we did not observe any morphologically visible skin lesions at the thoracic or lumbar level in 10-month-old uninjured Nf1-KO mutants (FIG. 11G and data not shown). The accumulation of traced cells in this region was limited and corresponded to micro-cNFs (FIG. 11H, K, K'). Furthermore, in our original Nf1-KO cohort, morphologically visible lesions were rare at the thoracic level (4 animals out of 26) and only found in aging individuals (17.5±3.6 months). Finally, while the thickness of the skin in the uninjured mutants in the lumbar region was typical of early stage micro-NFs (FIG. 11K), it was increased in the same region in injured mutants (FIG. 11J), consistent with cNF stage. Skin thickness reached an unprecedented level in the thoracic region of the injured mutants, with a dramatic expansion of the number of traced cells (FIG. 11I). Together these observations strongly support the idea that skin injury accelerates the progression of micro-cNFs to full-blown cNFs. This effect, although less intense, is also observed at a long distance from the injury site, suggesting that diffusible factors are involved and raising the possibility that the inflammatory response might be a key element in tumour progression.

Subepidermal Glia are the Likely Cell Type at the Origin of Cutaneous Neurofibroma It is striking that mice subjected to targeted Nf1 inactivation in Krox20-positive BC cells or Dhh-positive SC precursors develop pNFs, but never diffuse cNFs (Wu et al., 2008). A likely explanation is that the BC derivatives that migrate into the skin and participate in development of cNFs do not activate these two genes. To test this hypothesis, in vivo fate mapping and characterisation of derivatives of either Krox20- or Dhh-expressing progenitors in the adult skin was achieved by morphological and molecular analysis of TOM-positive cells from $Krox20^{Cre}$, $R26^{tdTom}$ and $Dhh^{Cre}$, $R26^{tdTom}$ adult animals. In $Krox20^{Cre}$, $R26^{tdTom}$ animals, the TOM-positive cells in the skin correspond to the rare S100+/MBP+ mSCs, NG2+ pericytes and previously described keratinocytes and hair follicle cells (FIG. 12A-B"). Notably, traced nmSCs were never observed. Expression of TOM in mSCs is likely to reflect Krox20 locus activation in mSC precursors around E15.5, rather than a BC origin of these cells.

Analysis of $Dhh^{Cre}$, $R26^{tdTom}$ adult skin revealed that a majority of mSCs and nmSCs were traced in the hypodermis (FIG. 12F and data not shown). In the dermis, TOM+ cells corresponded to various glial and non-glial derivatives (FIG. 12C-E, G). However, subepidermal glia, unsheathing nociceptive fibres at the dermis/epidermis boundary and melanocytes were not traced, in stark contrast to the situation in $Prss56^{Cre}$, $R26^{tdTom}$ skin (FIG. 12C, H and data not shown). Together these observations indicate that Prss56-, Krox20- and Dhh-traced populations give rise to overlapping and distinct types of glial populations in the skin (summarised in FIG. 12J). Among them, the only cell type uniquely derived from Prss56-positive cells is the subepidermal glia. As diffuse cNFs do not develop upon conditional Nf1 loss in Krox20- and Dhh-traced lineages, subepidermal SCs are likely to be the cell type at the origin of cutaneous neurofibromas.

$Prss56^{Cre}$, $NF1^{KO}$ Mice of the Invention Develop Eye Lesions that Often Accompanied NF1 Patients In addition to neurofibromas, young NF1 patients often develop eye lesions including optic glioma and hamartomas. Nf1-KO mice of the present invention develop retinal hamartomas characterized by a thickening of the outer plexiform layer. In these hamartomas numerous Tom-expressing, Nf1-KO perikarya were abnormally localized in the outer nuclear and plexiform layers, which normally does not contain any perikaryon. At the periphery of hamartomas Tom staining is restricted to most, but not all, Müller glial cells of the retina. In these hamartomas, a significant decrease of the acetylcholinesterase (AChE) mRNAs and corresponding protein were observed. AChE was described not only as an enzyme but also as an adhesive molecule, suggesting that the decrease amount of AChE described in the NF1 KO eye in retinal cells and in the remaining rows of photoreceptors nuclei might affect cell adhesion. Angiography analysis of the NF1 KO retinas reveal abnormal vascularisation potentially due to higher proliferation of endothelial cells. The retinal capillary plexus appears abnormally dense with some leaking arterioles, venules and capillaries. Oedema was observed in some areas of the NF1 KO retinas. Staining of flat mounted NF1 KO retinas with markers of endothelial cells (Isolectin B4 and PDGFRβ) further support abnormal vascularisation accompanied by the increased thickness of the retina. In conclusion, hamartomas present in the mice model of the invention are very similar to hamartomas observed in NF1 patients.

In $Prss56^{Cre}$ $NF1^{KO}$ Mice, Benign Neurofibromas Undergo Transformation into Aggressive MPNSTs In about 10% of NF1 patients, benign plexiform neurofibromas undergo transformation into aggressive malignant peripheral nerve sheath tumors (MPNST) with poor prognostic. Despite the availability of several genetically engineered mouse (GEM) models of NF1 developing plexiform tumors, in none of them spontaneous transformation of neurofibromas into MPNST was reported. In the NF1 mouse model of the present invention, about 10% of NF1 KO animals develop plexiform NFBs that undergo spontaneous transformation into MPNST-like tumors. Those fast-growing tumors develop mainly in males around 1 year of age and are localized at the lumbo-sacral level, often infiltrating the hindlimbs. Histological analysis of these tumors supports their malignant characteristics. Interestingly, in NF1 patients, development of MPNST is preceded by dysplastic period corresponding to progressive transformation of NFBs. Analysis of MPNST from NF1 KO mice of the present invention reveal the presence of similar transition stage, suggesting that this model fully recapitulate malignant transformation previously described in a subgroup of NF1 patients. To our knowledge, this is the first mouse model of spontaneous malignant transformation of neurofibromas. Such a model offers the possibility to uncover molecular mechanisms and actionable targets governing malignant transformation and can be used for screening of molecules blocking this mechanism. In addition, the presence of dysplasia in this model make possible identification of dysplastic markers that will be of great interest for the early detection of transforming neurofibromas.

$Prss56^{Cre}$ $NF1^{KO}$ Mice Shows Cognitive Dysfunctions Accompanied by Enhanced Oligodendrogenesis of Corpus Callosum About 70% of childrens diagnosed NF1 present cognitive dysfunctions including significant impairments in learning, behavior, and attention. The origin of the dysfunction remains largely unknown but several case reports described increased brain size accompanied by the increased thickness of corpus callosum. In the mouse model of the present invention, in addition to BC cells, Prss56 expression was reported in the adult neural stem cells present in the subventricular zone (SVZ) and dentate gyrus (DG). Interestingly, the NF1 KO mice of the invention shows cognitive dysfunction including lethargy and loss of attention. Interestingly, NF1 loss in both populations of neural stem cells have an important impact on their fate. In the SVZ, instead of generating neuroblasts that migrate along rostral migratory stream into olfactory bulb to generate neurons, they give rise to Olig2-expressing oligodendrocytes that detach from the dorsal wall of the SVZ and migrate and colonize corpus callosum. In the NF1 KO mice of the invention, corpus callosum is much thicker as it was observed in the NF1 patients. Majority of ectopic oligodendrocytes remain immature and do not undergo myelination. Similar phenotype was observed in the DG. Instead of generating neuroblasts, then interneurons that participate to neo-neurogenesis of the hippocampus, NF1 KO stem cells give rise to oligodendrocytes that emigrate from the DG to colonize different layers of the cortex. These observations suggest that these two phenotypes could be at the origin of the cognitive alterations described above. In addition to neurofibromas, the model of the invention successfully recapitulates cognitive dysfunctions similar to those described in NF1 patients.

The invention claimed is:

1. A transgenic mouse model of Neurofibromatosis type 1, wherein the genome of the mouse comprises:
   i) an insertion into one but not both alleles of an endogenous PRSS56 coding sequence of a nucleic acid sequence encoding Cre recombinase, wherein the nucleic acid sequence encoding Cre recombinase and an endogenous PRSS56 coding sequence are each operably linked to an endogenous PRSS56 promoter; and
   ii) a) two floxed NF1 alleles; or b) one floxed NF1 allele and one inactivated NF1 allele,
   wherein:
   cells of the mouse that express PRSS56 and derivatives thereof have an inactivated NF1 gene, and
   the mouse has or will have cutaneous and plexiform neurofibromas.

2. The transgenic mouse of claim 1, wherein cells of the mouse that express PRSS56 or derivatives thereof are boundary cap cells.

3. The transgenic mouse of claim 1, wherein cells of the mouse that express PRSS56 or derivatives thereof are non-myelinating Schwann cells, myelinating Schwann cells, endoneurial fibroblasts without basal lamina, melanocytes, dermal stem cells with neurogenic and gliogenic potential, satellite glial cells, nociceptive dorsal root ganglia (DRG) neurons, mechanoceptive DRG neurons, or proprioceptive DRG neurons.

4. The transgenic mouse of claim 1, wherein the genome of the mouse comprises a reporter coding sequence operably linked to an endogenous ROSA26 promoter.

5. A method for obtaining a cutaneous or plexiform neurofibroma (NFB) in vitro, the method comprising:
   a) isolating cells that express PRSS56 or derivatives thereof with an inactivated NF1 gene from the transgenic mouse of claim 1; and
   b) culturing the cells isolated in step a) such that a cutaneous or plexiform NFB is obtained.

6. A method for identifying a compound that impairs development of a cutaneous or plexiform neurofibroma (NFB), the method comprising:
   a) administering a compound to the cutaneous or plexiform NFB obtained in claim 5; and
   b) determining whether the compound impairs development of the cutaneous or plexiform NFB.

7. A method for identifying a compound that impairs development of a cutaneous or plexiform neurofibroma (NFB), the method comprising:
   A) administering a compound to a transgenic mouse model of Neurofibromatosis type 1, wherein the genome of the mouse comprises:
      i) an insertion into one but not both alleles of an endogenous PRSS56 coding sequence of a nucleic acid sequence encoding Cre recombinase, wherein the nucleic acid sequence encoding Cre recombinase and an endogenous PRSS56 coding sequence are each operably linked to an endogenous PRSS56 promoter; and
      ii) a) two floxed NF1 alleles; or b) one floxed NF1 allele and one inactivated NF1 allele,
   wherein:
   cells of the mouse that express PRSS56 or derivatives thereof have an inactivated NF1 gene, and the mouse has or will have a cutaneous or plexiform neurofibroma (NFB); and B) determining whether the compound impairs development of the cutaneous or plexiform NFB.

\* \* \* \* \*

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Prss56 primer (Forward)

<400> SEQUENCE: 1
gtcacaatcc ccgagaacag                                                   20

<210> SEQ ID NO 2
<211> LENGTH: 20
<212> TYPE: DNA
<213> ORGANISM: Artificial Sequence
<220> FEATURE:
<223> OTHER INFORMATION: Prss56 primer (Reverse)

<400> SEQUENCE: 2
ctcgctgaat agccgctaac                                                   20

<210> SEQ ID NO 3
<211> LENGTH: 20
<212> TYPE: DNA
<213> ORGANISM: Artificial Sequence
<220> FEATURE:
<223> OTHER INFORMATION: Prss56 primer (Forward)

<400> SEQUENCE: 3
ggtcttcagt ggcctagtgg                                                   20

<210> SEQ ID NO 4
<211> LENGTH: 20
<212> TYPE: DNA
<213> ORGANISM: Artificial Sequence
<220> FEATURE:
<223> OTHER INFORMATION: Prss56 primer (Reverse)

<400> SEQUENCE: 4
agcctctgtc cttgatcagc                                                   20

<210> SEQ ID NO 5
<211> LENGTH: 20
<212> TYPE: DNA
<213> ORGANISM: Artificial Sequence
<220> FEATURE:
<223> OTHER INFORMATION: Prss56 primer (Forward)

<400> SEQUENCE: 5
cctagcgctc caacagtgtc                                                   20

<210> SEQ ID NO 6
```

-continued

```
<210> SEQ ID NO 6
<211> LENGTH: 20
<212> TYPE: DNA
<213> ORGANISM: Artificial Sequence
<220> FEATURE:
<223> OTHER INFORMATION: Prss56 primer (Reverse)

<400> SEQUENCE: 6
agtgctcagc tgggatctgt                                               20

<210> SEQ ID NO 7
<211> LENGTH: 20
<212> TYPE: DNA
<213> ORGANISM: Artificial Sequence
<220> FEATURE:
<223> OTHER INFORMATION: Prss56 primer (Forward)

<400> SEQUENCE: 7
atgacctggc cttggtacag                                               20

<210> SEQ ID NO 8
<211> LENGTH: 20
<212> TYPE: DNA
<213> ORGANISM: Artificial Sequence
<220> FEATURE:
<223> OTHER INFORMATION: Prss56 primer (Reverse)

<400> SEQUENCE: 8
gacaggtgtc tgcactgagc                                               20

<210> SEQ ID NO 9
<211> LENGTH: 343
<212> TYPE: PRT
<213> ORGANISM: Enterobacteria phage P1
<220> FEATURE:
<223> OTHER INFORMATION: Cre recombinase

<400> SEQUENCE: 9
```

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

```
Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

<210> SEQ ID NO 10
<211> LENGTH: 1053
<212> TYPE: DNA
<213> ORGANISM: Artificial Sequence
<220> FEATURE:
<223> OTHER INFORMATION: Cre recombinase (cDNA)

<400> SEQUENCE: 10

```
atgcccaaga agaagaggaa ggtgtccaat ttactgaccg tacaccaaaa tttgcctgca      60
ttaccggtcg atgcaacgag tgatgaggtt cgcaagaacc tgatggacat gttcagggat     120
cgccaggcgt tttctgagca tacctggaaa atgcttctgt ccgtttgccg gtcgtgggcg     180
gcatggtgca agttgaataa ccggaaatgg tttcccgcag aacctgaaga tgttcgcgat     240
tatcttctat atcttcaggc gcgcggtctg gcagtaaaaa ctatccagca aactttgggc     300
cagctaaaca tgcttcatcg tcggtccggg ctgccacgac caagtgacag caatgctgtt     360
tcactggtta tgcggcggat ccgaaaagaa aacgttgatg ccggtgaacg tgcaaaacag     420
gctctagcgt tcgaacgcac tgatttcgac caggttcgtt cactcatgga aaatagcgat     480
cgctgccagg atatacgtaa tctggcattt ctggggattg cttataacac cctgttacgt     540
atagccgaaa ttgccaggat cagggttaaa gatatctcac gtactgacgg tgggagaatg     600
ttaatccata ttggcagaac gaaaacgctg gttagcaccg caggtgtaga aaggcactt      660
agcctggagg taactaaact ggtcgagcga tggatttccg tctctggtgt agctgatgat     720
ccgaataact acctgttttg ccgggtcaga aaaaatggtg ttgccgcgcc atctgccacc     780
agccagctat caactcgcgc cctggaaggg atttttgaag caactcatcg attgatttac     840
ggcgctaagg atgactctgg tcagagatac ctggcctggt ctggacacag tgcccgtgtc     900
ggagccgcgc gagatatggc ccgcgctgga gtttcaatac cggagatcat gcaagctggt     960
ggctggacca atgtaaatat tgtcatgaac tatatccgta acctggatag tgaaacaggg    1020
gcaatggtgc gcctgctgga agatggcgat tag                                 1053
```

<210> SEQ ID NO 11

```
<211> LENGTH: 34
<212> TYPE: DNA
<213> ORGANISM: Enterobacteria phage P1
<220> FEATURE:
<223> OTHER INFORMATION: loxP
<220> FEATURE:
<221> NAME/KEY: variation
<222> LOCATION: 14
<223> OTHER INFORMATION: /note="n is any of A, C, G or T"
<220> FEATURE:
<221> NAME/KEY: variation
<222> LOCATION: 15
<223> OTHER INFORMATION: /note="n is any of A, C, G or T"
<220> FEATURE:
<221> NAME/KEY: variation
<222> LOCATION: 16
<223> OTHER INFORMATION: /note="n is any of A, C, G or T"
<220> FEATURE:
<221> NAME/KEY: variation
<222> LOCATION: 19
<223> OTHER INFORMATION: /note="n is any of A, C, G or T"
<220> FEATURE:
<221> NAME/KEY: variation
<222> LOCATION: 20
<223> OTHER INFORMATION: /note="n is any of A, C, G or T"
<220> FEATURE:
<221> NAME/KEY: variation
<222> LOCATION: 21
<223> OTHER INFORMATION: /note="n is any of A, C, G or T"

<400> SEQUENCE: 11
ataacttcgt atannntann ntatacgaag ttat                              34

<210> SEQ ID NO 12
<211> LENGTH: 34
<212> TYPE: DNA
<213> ORGANISM: Enterobacteria phage P1
<220> FEATURE:
<223> OTHER INFORMATION: loxP

<400> SEQUENCE: 12
ataacttcgt ataatgtatg ctatacgaag ttat                              34

<210> SEQ ID NO 13
<211> LENGTH: 20
<212> TYPE: DNA
<213> ORGANISM: Artificial Sequence
<220> FEATURE:
<223> OTHER INFORMATION: Prss56Cre knock-in primer (Forward)

<400> SEQUENCE: 13
caggtgaggt gcggaccatt                                              20

<210> SEQ ID NO 14
<211> LENGTH: 25
<212> TYPE: DNA
<213> ORGANISM: Artificial Sequence
<220> FEATURE:
<223> OTHER INFORMATION: Prss56Cre knock-in primer (Reverse)

<400> SEQUENCE: 14
acggaaatcc atcgctcgac cagtt                                        25

<210> SEQ ID NO 15
<211> LENGTH: 20
<212> TYPE: DNA
<213> ORGANISM: Artificial Sequence
<220> FEATURE:
<223> OTHER INFORMATION: Beta-actin primer (forward)

<400> SEQUENCE: 15
```

```
tgttaccaac tgggacgaca                                                  20

<210> SEQ ID NO 16
<211> LENGTH: 20
<212> TYPE: DNA
<213> ORGANISM: Artificial Sequence
<220> FEATURE:
<223> OTHER INFORMATION: Beta-actin primer (reverse)

<400> SEQUENCE: 16
ggggtgttga aggtctcaaa                                                  20

<210> SEQ ID NO 17
<211> LENGTH: 20
<212> TYPE: DNA
<213> ORGANISM: Artificial Sequence
<220> FEATURE:
<223> OTHER INFORMATION: Nf1 primer (forward)

<400> SEQUENCE: 17
gcttccctca gaacagcatc                                                  20

<210> SEQ ID NO 18
<211> LENGTH: 21
<212> TYPE: DNA
<213> ORGANISM: Artificial Sequence
<220> FEATURE:
<223> OTHER INFORMATION: Nf1 primer (reverse)

<400> SEQUENCE: 18
gcccctttca attctaggtg g                                                21
```